US006331562B1

(12) United States Patent
Bhagwat et al.

(10) Patent No.: US 6,331,562 B1
(45) Date of Patent: Dec. 18, 2001

(54) COMPOUNDS AND METHODS FOR MODULATION OF ESTROGEN RECEPTORS

(75) Inventors: Shripad S. Bhagwat; Jeffrey A. McKie; Sak Khammungkhune, all of San Diego, CA (US)

(73) Assignee: Signal Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/611,156

(22) Filed: Jul. 6, 2000

Related U.S. Application Data

(63) Continuation of application No. 09/492,939, filed as application No. PCT/US99/31290 on Dec. 30, 1999, and a continuation-in-part of application No. 09/475,776, filed on Dec. 30, 1999, now abandoned.
(60) Provisional application No. 60/114,472, filed on Dec. 30, 1998.

(51) Int. Cl.$^7$ .......................... A61K 31/37; A61P 35/00; C07D 311/12

(52) U.S. Cl. .................. 514/457; 514/456; 546/196; 548/525; 549/289

(58) Field of Search .................. 548/525; 549/289; 514/456, 457

(56) References Cited

U.S. PATENT DOCUMENTS 5,716,983    2/1998    Friebe et al. .

FOREIGN PATENT DOCUMENTS

| 43 23 409 A1 | 1/1995  | (DE) . |
| 0 842 661 A2 | 5/1998  | (EP) . |
| WO 96/21656  | 7/1996  | (WO) . |
| WO 96/31206  | 10/1996 | (WO) . |
| WO 00/39120  | 7/2000  | (WO) . |

OTHER PUBLICATIONS

Ray et al, *Chemical Abstracts*, vol 107, No. 70964, 1987.*
Alonzi et al., 1998, "Interleukin 6 Is Required for the Development of Collagen–Induced Arthritis", J. Exp. Med. 187: 461–468.
Barkem et al., 1998, "Differential response of estrogen receptor α and estrogen receptor β to partial estrogen agonists/antagonists," Mol. Pharmacol. 54: 105–112.
Berrie et al., 1968, "Studies on Lettuce Seed Germination–I.: Coumarin Induced Domancy", Phytochemistry 7: 567–573.
Beyer and Raab, 1998, "Nongenomic effects of oestrogen: embryonic mouse midbrain neurones respond with a rapid release of calcium from intracellular stores", European Journal of Neuroscience 10: 255–262.
Bodine et al., 1998, "Estrogen Receptor–α Is Developmentally Regulated during Osteoblast Differentiation and Contributes to Selective Responsiveness of Gene Expression", Endocrinology 139: 2048–2057.

Borselllno et al., 1996, "Effects of an IL–6 receptor super–antagonist (IL–6R SAnt 7) on the growth and sensitivity to etoposide (VP–16) of the hormone resistant and IL–6–secreting prostate tumor PC–3 cell line", Proc. Amer. Assoc. Cancer Res. 37: 410–411 (abstract #2801).
Brandenberger et al., 1998, "Estrogen Receptor Alpha (ER–α) and Beta (ER–β) mRNAs in Normal Ovary, Ovarian Serous Cystadenocarcinoma and Ovarian Cancer Cell Lines: Down–Regulation of ER–β in Neeoplastic Tissues", J. of Clin. Endocrinology and Metabolism 83: 1025–1028.
Brandt et al., 1986, "Inhibition of Glyoxalase 1 In Vitro by Coumarin and Coumarin Derivatives", Int'L J. of Quantum Chemistry: Quantum Biology Symposium 13: 155–165.
Buu–Hoi et al., 1954, "Bz–hydroxylated–3–aryl–and 3,4–diaryl–coumarins", J. Org. Chem. 19: 1548–1552.
Chang and Prins, 1999, "Estrogen Receptor–β: Implications for the Prostate Gland", The Prostate 40: 115–124.
Clinton and Hua, 1997, "Estrogen action in human ovarian cancer", Critical Reviews in Oncology/Hematology 25: 1–9.
Cooke et al., 1998, "Mechanism of Estrogen Action: Lessons from the Estrogen Receptor–α Knockout Mouse", Biology of Reproduction 59: 470–475.

(List continued on next page.)

Primary Examiner—Robert W. Ramsuer
(74) Attorney, Agent, or Firm—Pennie & Edmonds LLP

(57) ABSTRACT

Compounds that modulate gene expression through the estrogen receptor (ER) are disclosed having the following structure, as well as pharmaceutical compositions containing the same:

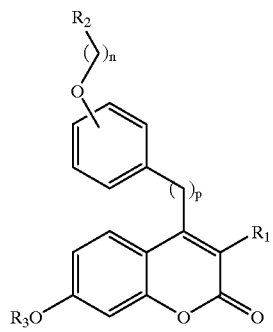

wherein $R_1$, $R_2$, $R_3$, n and p are as defined here. In a specific embodiment, the compounds are selective modulators for Er-β over ER-α. Methods are also disclosed for modulating ER-β in cells and/or tissues expressing the same, including cells and/or tissues that preferentially express ER-β. More generally, methods for treating estrogen-related conditions are also disclosed, including conditions such as is breast cancer, testicular cancer, osteoporosis, endometriosis, cardiovascular disease, hypercholesterolemia, prostatic hypertrophy, prostatic carcinomas, obesity, hot flashes, skin effects, mood swings, memory loss, urinary incontinence, hairloss, cataracts, natural hormonal imbalances, and adverse reproductive effects associated with exposure to environmental chemicals.

63 Claims, 5 Drawing Sheets

OTHER PUBLICATIONS

Couse et al., 1997, "Tissue Distribution and Quantitative Analysis of Estrogen Receptor–α (ERa) and Estrogen Receptor–β (Erβ) Messenger Ribonucleic Acid in the Wild–Type and Era–Knockout Mouse", Endocrinology 138: 4613–4621.

Das et al., 1997, "Estrogenic responses in estrogen receptor–α deficient mice reveal a distinct estrogen signaling pathway", Proc. Natl. Acad. Sci. USA 94: 12786–12791.

Duan et al., 1998, "Estrogen–Induced c–fos Protooncogene Expression in MCF–7 Human Breast Cancer Cells; Rule of Estrogen Receptor Sp1 Complex Formation", Endocrinology 139: 1981–1990.

Enmark et al., 1997, "Human Estrogen Receptor β–Gene Structure, Chromosomal Localization, and Expression Pattern", J. of Clin. Endocrinology and Metabolism 82: 4258–4265.

Eustace et al., 1993, "Interleukin–6 (IL–6) Functions as an Autocrine Growth Factor in Cervical Carcinomas in Vitro", Gynecologic Oncology 50: 15–19.

Farhat et al., 1996, "The vascular protective effects of estrogen", The FASEB Journal 10:615 621.

Garrett et al., 1997, "A Murine Model of Human Myeloma Bone Disease", Bone 20: 515–520.

Girasole et al., 1992, "17 β Estradiol Inhibits Interleukin–6 Production by Bone Marrow–derived Stromal Cells and Osteoblasts In Vitro": A Potential Mechanism for the Antiosteoporotic Effect of Estrogens, J. of Clin. Investigation859: 883–891.

Grese et al., 1997, "Structure–activity relationships of selective estrogen modulators: modifcations to the 2–arylbenzothiophene core of raloxifene", *J. Med. Chem.* 40: 146–147.

Gu et al., 1999, "Rapid Action of 17 β–Estradiol on Kainate–Induced Currents in Hippocamal Neurons Lacking Intracellular Estrogen Receptors", Endocrinology 140:660–666.

Gupta et al., 1985, "7–hydroxy 4–phenyl–3(4–hydroxyphenyl)–coumarin—a new interceptive agent", Ind. J. Exp. Biol. 23:638–641.

Gustafsson, 1998, "Therapeutic potential of selective estrogen receptor modulators", Curr. Opin. Chem. Biol. 2(4): 508–511.

Hata et al., 1998, "Role of Estrogen and Estrogen–Related Growth Factor in the Mechanism of Hormone Dependency of Endometrial Carcinoma Cells," Oncology 55(suppl 1): 35–44.

Hughes et al., 1996, "Estrogen promotes apoptosis of murine osteoclasts mediated by TGF β", Nature Medicine 2: 1132–1136.

Iafrati et al., 1997, "Estrogen inhibits the vascular injury response in estrogen receptor α–deficient mice", Nature Medicine 3: 545–546.

Iglesias et al., 1995, "Interleukin–6 and Interleukin–6 Soluble Receptor Regulate Proliferation of Normal Human Papillomavirus–immortalized, and Carcinoma–Derived Cervical Cells in Vitro", Am. J. of Pathology 146 944–952.

Improta–Brears et al., 1999, "Estrogen–induced activation of mitogen–activated protein kinase requires mobilization of intracellular calcium", *Proc. Natl. Acad. Sci. USA 96:* 4686–4691.

Jansson et al., 1994, "Estrogen induces a potent suppression of experimental autoimmune encephalomyelitis and collagen–induced arthritis in mice", Journal of Neuroimmunology 53: 203–207.

Jeltsch et al., 1987, "Structure of the human oestrogen responsive gene pS2", Nucleic Acids Research 15: 1401–1414.

Jilka et al., 1995, "Estrogen loss upregulates hematopoiesis in the mouse: A mediating role of IL–6", Experimental Hematology 23: 500–506.

Jilka et al., 1992, "Increased Osteoclast Development After Estrogen Loss: Mediation by Interleukin–6", Science 257:88–91.

Katzenellenbogen and Korach, 1997, "Editorial: A New Actor in the Estrogen Receptor Drama–Enter ER–β", Endocrinology 138; 861–862.

Ke et al., 1998, "Effects of CP–336, 156, a New, Nonsteroidal Estrogen Agonist/Antagonist, on Bone, Serum Cholesterol, Uterus, and Body Composition in Rat Models", Endocrinology 139: 2068–2076.

Khalkin and Rakova, 1968, "Ultraviolet Spectra of Some 6,7–and 7,8–Dihydroxycoumarins", J. of Applied Spectroscopy 8: 640–642.

Kimble et al., 1996, "Estrogen Deficiency Increases the Ability of Stromal Cells to Support Murine Osteoclastogenesis via an Interleukin–1–and Tumor Necrosis Factor–mediated Stimulation of Macrophage Colony–stimulating Factor Production", J. of Biol. Chem. 271: 28890–28897.

Kimble et al., 1995, "Simultaneous Block of Interleukin–1 and Tumor Necrosis Factor is Required to Completely Prevent Bone Loss in the Early Postovariectomy Period", Endocrinology 136: 3054–3061.

Klein et al., 1991, "Murine Anti–Interleukin–5 Monoclonal Antibody Therapy for a Patient With Plasma Cell Leukemia", Blood 78: 1198–1204.

Klein et al., 1989, "Paracrine Rather Than Autocrine Regulation of Myeloma–Cell Growth and Differentiation by Interleukin–6", Blood 73: 517–526.

Koo et al., 1992, "Interleukin–6 and renal cell cancer: production, regulation, and growth effects", Cancer Immunol. Immunother. 35: 97–105.

Korach, 1994, "Insights from the Study of Animals Lacking Functional Estrogen Receptor", Science 266: 1524–1527.

Krege et al., 1998, "Generation and reproductive phenotypes of mice lacking estrogen receptor β", Proc. Natl. Acad. Sci. USA 95: 15677–15682.

Kuiper et al., 1996, "Cloning of a novel estrogen receptor expressed in rat prostate and ovary", Proc. Natl. Acad. Sci. USA 93:5925–5930.

Laflamme et al., 1998, "Expression and Neuropeptidergic Characterization of Estrogen Receptors (Erα and Erβ) throughout the Rat Brain: Anatomical Evidence of Distinct Roles of Each Subtype", J. of Neurobiology 36:357–378.

Lednicer et al., 1965, "Mammalian Antifertility Agents. II. Basic Ethers of 3,4–Diphenylcoumarins", J. Medical Chemistry 8: 725–726.

Leisten et al., 1990, "Interleukin–6 serum levels correlate with footpad swelling in adjuvant–induced arthritic Lewis rats treated with cyclosporin A and indomethacin", Clin. Immunol. Immunopathol. 56: 108–115.

Martinez–Maza, 1992, "IL6 and AIDS", Research in Immunology 7: 764–769.

McGuire, 1978, "Steroid Receptors in Human Breast Cancer", Cancer Ressearch 38: 4289–4291.

Medlock et al., 1997, "Effects of Toremifene on Neonatal Rat Uterine Growth and Differentiation", Biology of Reproduction 56: 1239–1244.

Micheli et al., 1962, "Coumestrol, Plant Pheonolics, and Synthetic Estrogens: a Correlation of Structure and Activity", Steroids 5: 321–336.

Mosselman et al., 1996, "Erβ: identification and characterization of a novel human estrogen receptor", FEBS Letters 392: 49–53.

Nilsson et al., "Erβ: a Novel Estrogen Receptor Offers the Potential for New Drug Development", TEM 9: 387–395.

Ogawa et al., 1997, "Behavorial effects of estrogen receptor gene disruption in male mice", Proc. Natl. Acad. Sci. USA 94: 1476–1481.

Ohshima et al., 1998, "Interleukin 6 plays a key role in the development of antigen–induced arthritis", Proc. Natl. Acad. Sci. USA 95: 8222–8226.

Okamoto et al., 1997, "Autocrine Effect of Androgen on Proliferation of an Androgen Responsive Prostatic Carcinoma Cell Line, LNCAP: Role of Interleukin–6", Endocrinology 138: 5071–5074.

Okamoto et al., 1997, "Interleukin–6 as a Paracrine and Autocrine Growth Factor In Human Prostatic Carcinoma Cells in Vitro", Cancer Research 57: 141–146.

Pacifici, 1996, "Estrogen, Cytokines, and Pathogenesis of Postmenopausal Osteoporosis", J. of Bone and Mineral Research 11: 1043–1051.

Paech et al., 1997, "Differential ligand activation of estrogen receptors Erα and Erβ at AP1 sites", Science 277: 1508–1510.

Parfitt et al., 1996, "A New Model for the Regulation of Bone Resorption, with Particular Reference to the Effects of Biphosphonates" J. of Bone and Mineral Research 11: 150–159.

Passeri et al., 1993, "Increased Interleukin–6 Production by Murine Bone Marrow and Bone Cells after Estrogen Withdrawal", Endocrinology 133: 822–828.

Poll et al., 1994, "Interleukin–6 deficient mice are protected from bone loss caused by estrogen depletion", EMBO Journal 13: 1189–1196.

Pollard and Martin, 1968, "The Ostrogenic and Anti–Oestrogenic Activity of Some Synthetic Steroids and Non– Steroids", Steroids 11: 897–899.

Rao and Srimannarayana, 1981, "A Novel and Convenient Synthesis of 3–Phenylcoumarins", Synthesis 11:887–888.

Ray et al., 1987, "Enhanced Antifertility Activity of Non–Steroidal Molecules with 3–n–Butylamino–2–Hydroxypropyloxy Side Chain", Contraception 35: 283–287.

Rissman et al., 1997, "Estrogen Receptor Function as Revealed by Knockout Studies: Neuroendrocrine and Behavioral Aspects", Hormones and Behavior 31:232–243.

Riseman et al., 1997, "Estrogen Receptors are Essential for Female Sexual Receptivity", Endocrinology 138: 507–510.

Rohlff et al., 1998, "Prostate Cancer Cell Growth Inhibition by Tamoxifen is Associated with Inhibition of Protein Kinase C and Induction of p21 $^{wa{f1}/dp1}$", The Prostate 37: 51–59.

Rosati et al., 1998, "Discovery of preclinical pharmacology of a novel, potent, nonsteroidal estrogen receptor agonist/antagonist, CP–336156, a diaryltetrahydronopthalene", J. Med. Chem. 41:2928–2931.

Salman et al., 1986, "3,4–Diaryl–Coumarins, Chromenes and Chromans as Novel Anti–Inflammatory Agents", Indian J. Pharm. Sci., 49: 43–47.

Sar and Welsch, 1999, "Differential Expression of Estrogen Receptor–β and Estrogen Receptor–α in the Rat Ovary", Endocrinology 140: 963–971.

Shughrue et al., 1997, "Comparative Distribution of Estrogen Receptor–α and –β mRNA in the Rat Central Nervous System", J. of Comp. Neurology 388: 507–525.

Shughrue et al., 1997, "The Distribution of Estrogen Receptor–β mRNA in Forebrain Regions of the Estrogen Receptor–α Knockout Mouse", Endocrinology 138: 5649–5652.

Shughrue et al., 1997, "Responses in the brain of estrogen receptor α–disrupted mice", Proc. Natl. Acad. Sci. USA 94: 11008–11012.

Siegall et al., 1990, "Expression of the Interleukin 6 Receptor and Interleukin 6 in Prostate Carcinoma Cells", Cancer Research 50: 7786–7788.

Simpson et al., 1998, "Estrogen Regulation of Transforming Growth Factor–α in Ovarian Cancer", J. Steroid Biochem. Molec. Biol. 64: 137–145.

Stein and Yang, 1995, "Repression of the Interleukin 6 Promoter by Estrogen Receptor Is Medated by NF–kB and C/EBPβ", Molecular and Cellular Biology 15: 49/1–4979.

Sun et al., 1999, "Novel ligands that function as selective estrogens or antiestrogens for estrogen receptor–α or estrogen receptor–β", Endocrinol. 140: 800–804.

Suzuki et al., 1996, "Calcitonin–Induced Changes in the Cytoskeleton Are Mediated by a Signal Pathway Associated with Protein Kinase A in Osteoclasts", Endocrinology 137: 4685–4690.

Tartour et al., 1994, "Analysis of Interleukin 6 Gene Expression in Cervical Neoplasia Using a Quantitative Polymerase Chain Reaction Assay: Evidence for Enhanced Interleukin 6 Gene Expression in Invasive Carcinoma", Cancer Research 64: 6243–6248.

Tremblay et al., 1998, "EM–800, a novel antiestrogen, acts as a pure antagonist of the transcriptional functions of estrogen receptors α and β", Endocrinol. 139: 111–118.

Tsukamoto et al., 1992, "Interleukin–6 in Renal Cell Carcinoma", Journal of Urology 148: 1778–1782.

Turner et al., 1998, "Differential Responses of Estrogen Target Tissues in Rats Including Bone to Clomiphene, Enclomlphene, and Zuclomiphone", Endocrinology 139:3712–3720.

Verma et al., 1993, "Synthesis of 3–aryl–1–(4–methoxyphenyl)–2–[4–(2–substituted aminoethoxy)–phenyl]–2–propen–1–ones and benzopyran derivatives", Indian Journal of Chemistry 328: 239–243.

Wanl et al., 1975, "Flavonoids 8 Synthesis and Antifertility and Estrogen Receptor Binding Activities of Coumarins and Δ3–Isoflavenes", J. of Medicinal Chemistry 18: 982–905.

Watters et al., 1997, "Rapid Membrane Effects of Steroids in Neuroblastoma Cells: Effects of Estrogen on Mitogen Activated Protein Kinase Signalling Cascade and c–fos Immedlate Early Gene Transcription", Endocrinology 138: 4030–4033.

Weissglas et al., 1997, "The Role of Interleukin–6 in the Induction of Hypercalcemia in Renal Cell Carcinoma Transplanted into Nude Mice", Endocrinology 138: 1879–1885.

Wendling et al., 1993, "Treatment of Severe Rheumatoid Arthritis by Anti–Interleukin 6 Monoclonal Antibody", J. of Rheumatology 20:259–262.

Yamashita et al., 1998, "Endocrine Therapy in Pancreatic Carcinoma", Oncology 55 (suppl 1): 17–22.

Zhang et al., 1989, "Interleukin–6 Is a Potent Myeloma–Cell Growth Factor in Patients With Aggressive Multiple Myeloma", Blood 74: 11–13.

* cited by examiner

COMPOUNDS AND METHODS FOR MODULATION OF ESTROGEN RECEPTORS

CROSS-REFERENCE TO RELATED APPLICATION

This application is a continuation-in-part of U.S. application Ser. No. 09/492,939, filed Jan. 27, 2000, which is (i) a continuation-in-part of International Application No. PCT/US99/31290, filed Dec. 30, 1999, published under PCT Article 21(2) in English as International Publication No. WO 00/39120, which claims the benefit of U.S. Provisional Application No. 60/114,472, filed Dec. 30, 1998, and (ii) a continuation-in-part of application Ser. No. 09/475,776 filed Dec. 30, 1999, now abandoned, which claims the benefit of U.S. Provisional Application No. 60/114,472, filed Dec. 30, 1998 (each of which applications are hereby incorporated by reference in their entirety).

TECHNICAL FIELD

This invention is generally directed to estrogen antagonists and agonists, and to compounds for inhibiting cytokines, and more specifically to compounds which selectively modulate estrogen receptor-beta (ER-β) activity, as well as to pharmaceutical compositions and methods related thereto.

BACKGROUND OF THE INVENTION

The estrogen hormone has a broad spectrum of effects on tissues in both females and males. Many of these biological effects are positive, including maintenance of bone density, cardiovascular protection, central nervous system (CNS) function, and the protection of organ systems from the effects of aging. However, in addition to its positive effects, estrogen also is a potent growth factor in the breast and endometrium that increases the risk of cancer.

Until recently, it was assumed that estrogen binds to a single estrogen receptor (ER) in cells. As discussed below, this simple view changed significantly when a second ER (ER-β) was cloned (with the original ER being renamed ER-α), and when co-factors that modulate the ER response were discovered. Ligands can bind to two different ERs which, in the presence of tissue-specific co-activators and/or co-repressors, bind to an estrogen response element in the regulatory region of genes or to other transcription factors. Given the complexity of ER signaling, along with the tissue-specific expression of ER-α and ER-β and its co-factors, it is now recognized that ER ligands can act as estrogen agonists and antagonists that mimic the positive effects, or block the negative effects, of estrogen in a tissue-specific manner. This has given rise to the discovery of an entirely new class of drugs, referred to as Selective Estrogen Receptor Modulators or SERMs. These drugs have significant potential for the prevention and/or treatment of cancer and osteoporosis, as well as cardiovascular diseases and neurodegenerative diseases such as Alzheimer's Bone-resorbing diseases, such as osteoporosis, are debilitating conditions which affect a wide population, and to which there is only limited treatment. For example, osteoporosis affects about 50% of women, and about 10% of men, over the age of 50 in the United States. In individuals with osteoporosis. increased loss of bone mass results in fragile bones and, as a result., increased risk of bone fractures. Other bone-resorption diseases, such as Paget's disease and metastatic bone cancer, present similar symptoms.

Bone is a living tissue which contains several different types of cells. In healthy individuals, the amount of bone made by the osteoblastic cells is balanced by the amount of bone removed or resorbed by the osteoclastic cells. In individuals suffering from a bone-resorbing disease, there is an imbalance in the function of these two types of cells. Perhaps the most well known example of such an imbalance is the rapid increase in bone resorption experienced by postmenopausal women. Such accelerated bone lose is attributed to estrogen deficiency associated with menopause. However, the mechanism of how the loss of estrogen results in increased bone resorption has long been debated.

Recently, investigators have suggested that an increase in bone-resorbing cytokines, such as interleukin-1 (IL-1) and tumor necrosis factor (TNF), may be responsible for postmenopausal bone loss (Kimble et al., *J. Biol. Chem.* 271:28890–28897, 1996), and that inhibitors of these cytokines can partially diminish bone loss following ovariectomy in rodents (Pacifici, *J. Bone Miner Res.* 11:1043– 1051, 1996). Further, discontinuation of estrogen has been reported to lead to an increase in IL-6 secretion by murine bone marrow and bone cells (Girasole et al., *J. Clin. Invest.* 89:883–891, 1992; Jilka et al., Science 257:88–91, 1992; Kimble et al., *Endocrinology* 136:3054–3061, 1995; Passeri et al., *Endocrinology* 133:822–828, 1993), antibodies against IL-6 can inhibit the increase in osteoclast precursors occurring in estrogen-depleted mice (Girasole et al, supra), and bone loss following ovariectomy does not occur in transgenic mice lacking IL-6 (Poli et al., *EMBO J.* 13:1189–1196, 1994).

Existing treatments for slowing bone loss generally involves administration of compounds such as estrogen, bisphosphonates, calcitonin, and raloxifene. These compounds, however, are generally used for long-term treatments, and have undesirable side effects. Further, such treatments are typically directed to the activity of mature osteoclasts, rather than reducing their formation. For example, estrogen induces the apoptosis of osteoclasts, while calcitonin causes the osteoclasts to shrink and detach from the surface of the bone (Hughes et al., Nat. Med. 2:1132–1136, 1996; (Jilka et al., *Exp. Hematol.* 23:500–506, 1995). Similarly, bisphosphonates decrease osteoclast activity, change their morphology, and increase the apoptosis of osteoclasts (Parfitt et al., *J. Bone Miner* 11:150–159, 1996; Suzuki et al., *Endocrinology* 137:4685–4690, 1996).

Cytokines are also believed to play an important role in a variety of cancers. For example, in the context of prostate cancer, researchers have shown IL-6 to be an autocrine/paracrine growth factor (Seigall et al., *Cancer Res.* 50:7786, 1999). to enhance survival of tumors (Okamoto et al., *Cancer Res.* 57:141–146, 1997), and that neutralizing IL-6 antibodies reduce cell proliferation (Okamoto et al., *Endocrinology* 138:5071–5073, 1997; Borsellino et al., *Proc. Annu. Meet. Am. Assoc. Cancer Res.* 37:A2801, 1996). Similar results have been reported for IL-6 with regard to multiple myeloma (Martinez-Maza et al., *Res. Immunol.* 143:764–769, 1992; Kawano et al., *Blood* 73:517–526, 1989; Zhang et al., *Blood* 74:11–13, 1989; Garrett et al., *Bone* 20:515–520, 1997; and Klein et al., *Blood* 78:1198–12–4, 1991), renal cell carcinoma (Koo et all. *Cancer Immunol.* 3597–105, 1002: Tsukamoto et al., *J. Urol.* 148:1778–1782, 1992; and Weissglas et al., *Endocrinology* 138:1879–1885. 1997), and cervical carcinoma (Estuce et al., *Gynecol. Oncol.* 50:15–19, 1993; Tartour et al., *Cancer Res.* 54:6243–6248, 1994; and Iglesias et al., *Am. J. Pathology* 146:944–952, 1995).

Furthermore, IL-6 is also believed to be involved in arthritis, particularly in adjuvant-, collagen- and antigen-induced arthritis (Alonzi et al., *J. Exp. Med.* 187:146–148, 1998; Ohshima et al., *Proc. Natl. Acad. Sci. USA* 95:8222–8226, 1998; and Leisten et al., *Clin. Immunol. Immunopathol* 56:108–115, 1990), and anti-IL-6 antibodies have been reported for treatment of arthritis (Wendling et al., *J Rheumatol.* 20:259–262, 1993). In addition, estrogen has been shown to induce suppression of experimental autoimmune encephalomyelitis and collagen-induced arthritis in mice (Jansson et al., *Neuroimmunol.* 53:203–207, 1994).

As noted above, it had previously been assumed that estrogen binds to a single estrogen receptor (ER) in cells, causing conformational changes that result in release from heat shock proteins and binding of the receptor as a dimer to the so-called estrogen response element in the promoter region of a variety of genes. Further, pharmacologists have generally believed that non-steroidal small molecule ligands compete for binding of estrogen to ER, acting as either antagonists or agonists in each tissue where the estrogen receptor is expressed. Thus, such ligands have traditionally been classified as either pure antagonists or agonists. This is no longer believed to be correct.

Rather, it is now known that estrogen modulates cellular pharmacology through gene expression, and that the estrogen effect is mediated by estrogen receptors. As noted above, there are currently two estrogen receptors, ER-$\alpha$ and ER-$\beta$. The effect of estrogen receptor on gene regulation can be mediated by a direct binding of ER to the estrogen response element (ERE)-"classical pathway" (Jeltsch et al., *Nucleic Acids Res.* 15:1401–1414, 1987; Bodine et al., *Endocrinology* 139:2048–2057, 1998), binding of ER to other transcription factors such as NF-$\kappa$B. C/EBP-$\beta$ or AP-1-"non-classical pathway" (Stein et al., *Mol. Cell Biol.* 15:4971–4979, 1995; Paech et al., *Science* 277:1508–1510, 1997; Duan et al., *Endocrinology* 139:1981–1990, 1998), and through non-genomic effects involving ion channel receptors (Watters et al., *Endocrinology* 138:4030–4033, 1997; Improta-Brears et al., *Proc. Natl. Acad. Sci. USA* 96:4686–4691, 1999; Gu et al., *Endocrinology* 140:660–666, 1999; Beyer et al., *Eur. J. Neurosci.* 10:255–262, 1998).

Progress over the last few years has shown that ER associates with co-activators (e.g., ARC-1, CBP and SRA) and co-repressors (e,g., SMRT and N-CoR), which also modulate the transcriptional activity of ER in a tissue-specific and ligand-specific manner. In addition, evidence now suggests that the majority of estrogen-regulated genes do not have a classical estrogen response element. In such cases, ER interacts with the transcription factors critical for regulation of these genes. Transcription factors known to be modulated in their activity by ER include, for example, AP-1, NF$\kappa$B, C/EBP and Sp-1.

Given the complexity of ER signaling, as well as the various types of tissue that express ER and its co-factors, it is now believed that ER ligands can no longer simply be classified as either pure antagonists or agonists. Therefore, the term "selective estrogen receptor modulator" (SERM) has been coined. SERMs bind to ER, but may act as an agonist or antagonist of estrogen in different tissues and on different genes. For example, two of the most well known drugs that behave as SERMs are Tamoxifen and Raloxifene. Studies with these two compounds, as well as other SERMs now in development, have demonstrated that the affinity of a SERM for its receptor in many cases does not correlate with its biological activity. Therefore, ligand-binding assays traditionally used in screening for novel ER modulators have not distinguished between tissue-selectivity and agonist/antagonist behavior.

More recently, a second estrogen receptor, ER-$\beta$, has been identified and cloned (Katzenellenbogen and Korach *Endocrinology* 138, 861–2 (1997); Kuiper et al., *Proc. Natl. Acad. Sci. USA* 93, 5925–5930, 1996; Mosselman et al., *FEBS Lett.* 392, 49–53, 1996). ER-$\beta$, and the classical ER renamed ER-$\alpha$, have significantly different amino acid sequences in the ligand binding domain and carboxy-terminal transactivation domains (~56% amino acid identity), and only 20% homology in their amino-terminal transactivation domain. This suggests that some ligands may have higher affinity to one receptor over the other. Further, ligand-dependent conformational changes of the two receptors, and interaction with co-factors, will result in very different biological actions of a single ligand. In other words, a ligand that acts as an agonist on ER-$\alpha$ may very well serve as an antagonist on ER-$\beta$. An example of such behavior has been described by Paech et al. (*Science* 277, 1508–1510, 1997). In that paper, estrogen is reported to activate an AP-1 site in the presence of ER-$\alpha$, but to inhibit the same site in the presence of ER-$\beta$. In contrast, Raloxifene (Eli Lilly & Co.) and Tamoxifen and ICI-182,780 (Zeneca Pharmaceuticals) stimulate the AP-1 site through ER-$\beta$, but inhibit this site in the presence of ER-$\alpha$. Another example has been described by Sun et al. (*Endocrinology* 140, 800–4, 1999). In this paper, the R,R-enantiomer of a tetrahydrochrysene is reported to be an agonist on ER-$\alpha$, but a complete antagonist on ER-$\beta$, while the S,S-enantiomer is an agonist on both receptors.

Furthermore, ER-$\alpha$ and ER-$\beta$ have both overlapping and different tissue distributions, as analyzed predominantly by RT-PCR or in-situ hybridization due to a lack of good ER-$\beta$ antibodies. Some of these results, however, are controversial, which may be attributable to the method used for measuring ER, the species analyzed (rat, mouse, human) and/or the differentiation state of isolated primary cells. Very often tissues express both ER-$\alpha$ and ER-$\beta$, but the receptors are localized in different cell types. In addition, some tissues (such as kidney) contain exclusively ER-$\alpha$, while other tissues (such as uterus, pituitary and epidymis) show a great predominance of ER-$\alpha$ (Couse et al., *Endocrinology* 138, 4613–4621, 1997; Kuiper et al., *Endocrinology* 138, 863–870, 1997). In contrast, tissues expressing high levels of ER-$\beta$ include prostate, testis, ovaries and certain areas of the brain (Brandenberger et al., *J. Clin. Endocrinol. Metab.* 83, 1025–8, 1998; Enmark et al., *J Clinic. Endocrinol. Metabol.* 82, 4258–4265, 1997; Laflamme et al., *J. Neurobiol.* 36, 357–78, 1998; Sar and Welsch, *Endocrinology* 140, 963–71, 1999; Shughrue et al., *Endocrinology* 138, 5649–52, 1997a; Shughrue et al., *J. Comp. Neurol.* 388, 507–25, 1997b).

The development of ER-$\alpha$ (Korach, *Science* 266, 1524–1527, 1994) and ER-$\beta$ (Krege et al., *Proc. Natl. Acad. Sci. USA* 95, 15677–82. 1998) knockout mice further demonstrate that ER-$\beta$ has different functions in different tissues. For example, ER-$\alpha$ knockout mice (male and female) are infertile, females do not display sexual receptivity and males do not have typical male-aggressive behavior (Cooke et al., *Biol. Reprod.* 59, 470–5, 1998; Das et al., *Proc. Natl. Acad. Sci. USA* 94, 12786–12791, 1997; Korach, 1994; Ogawa et al., *Proc. Natl. Acad. Sci. USA* 94, 1476–81, 1997; Rissman et al., *Endocrinology* 138, 507–10, 1997a; Rissman et al., *Horm. Behav.* 31, 232–243, 1997b). Further, the brains of these animals still respond to estrogen in a pattern that is similar to that of wild type animals (Shughrue et al., *Proc. Natl. Acad. Sci. USA* 94, 11008–12, 1997c), and estrogen still inhibits vascular injury caused by mechanical damage (Iafrati et al., *nature Med.* 3, 545–8, 1997). In contrast, mice lacking the ER-$\beta$ develop normally, are fertile and exhibit normal sexual behavior, but have fewer and smaller litters than wild-type mice (Krege et al., 1998), have normal breast development and lactate normally. The reduction in fertility is believed to be the result of reduced ovarian efficiency, and ER-β is the predominant form of ER in the ovary, being localized in the granulosa cells of maturing follicles.

In summary, compounds which serve as estrogen antagonists or agonists have long been recognized for their significant pharmaceutical utility in the treatment of a wide variety of estrogen-related conditions, including conditions related to the brain, bone, cardiovascular system, skin, hair follicles, immune system, bladder and prostate (Barkhem et al., *Mol. Pharmacol.* 54, 105–12, 1998; Farhat et al., *FASEB J.* 10. 615–624, 1996; Gustafsson, Chem. Biol. 2, 508–11, 1998. Sun et al., 1999; Tremblay et al., *Endocrinology* 139, 111–118, 1998; Turner et al., *Endocrinology* 139, 3712–20, 1998). In addition, a variety of breast and non-breast cancer cells have been described to express ER, and serve as the target tissue for specific estrogen antagonists (Brandenberger et al., 1998; Clinton and Hua, *Crit. Rev. Oncol. Hematol.* 25, 1–9, 1997; Hata et al., *Oncology* 55 Suppl 1, 35–44. 1998; Rohlff et al., *Prostate* 37, 51–9, 1998; Simpson et al., *J Steroid Biochem Mol Biol* 64, 137–45, 1998; Yamashita et al., *Oncology* 55 Suppl 1. 17–22, 1998).

With the recent identification of the ER-β, and the recognition that ER-α and ER-β have different biological roles, ER-selective modulators would similarly possess significant clinical utility. Since ER-β is expressed strongly in a number of tissues including prostrate, bladder, ovary, testis, lung, small intestine, vascular endothelium, and various parts of the brain, compounds that selectively modulate ER-β would be of clinical importance in the treatment of a variety of diseases or conditions, such as prostate cancer, testicular cancer, cardiovascular diseases, neurodegenerative disorders, urinary incontinence, CNS, GI tract conditions, and bone and other cancers. Such compounds would have minimal effect on tissues that contains ER-α, and thus exhibit different side-effect profiles. For example, while estrogen replacement therapy is as associated with a variety of beneficial effects (such as bone protection, cardiovascular effect, prevention of hot flashes, dementia, bone metabolism, etc.), such therapy also has adverse effects (such as breast and endometrial cancer, thrombosis, etc.). Some of these adverse effects are believed to be mediated by ER-α or ER-β specific mechanisms. Thus. ER-β antagonists or agonists will display different therapeutic profiles compared to ER-α antagonists or agonists, and would be preferentially beneficial in tissues expressing high levels of ER-β (see, e.g., Nilsson et al., *TEM* 9, 387–395, 1998; Chang and Prins, *The Prostate* 40, 115–124, 1999). Furthermore, a number of investigators have shown that environmental chemicals and phytoestrogens preferentially interact with R-β by triggering biological responses similar to that of estrogen (see, e.g., Kuiper et al., *Endocrinology* 139, 4252–4263, 1998). Thus, compounds that antagonize ER-β would also be important in regulating interactions with chemicals, affecting health, reproductive capacity and the like.

In recent years a number of both steroidal and nonsteroidal compounds which interact with ER have been developed. For example, Tamoxifen was originally developed as an anti-estrogen and used for the treatment of breast cancer, but more recently has been found to act as a partial estrogen agonist in the uterus, bone and cardiovascular system. Raloxifene is another compound that has been proposed as a SERM, and has been approved for treatment of osteoporosis.

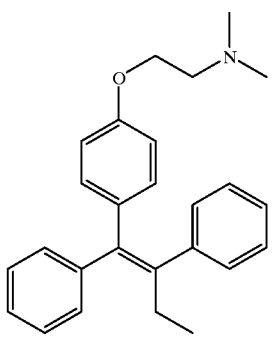

Tamoxifen

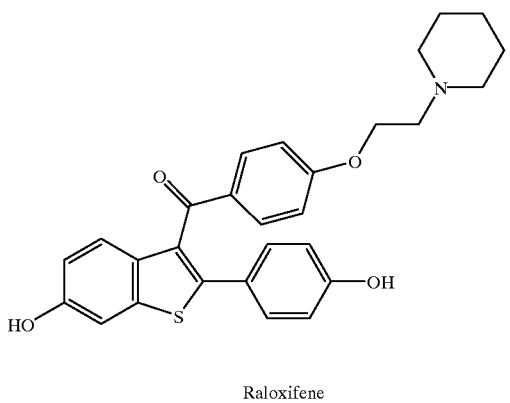

Raloxifene

Analogs of Raloxifene have also been reported (Grese et al., *J. Med. Chem.* 40:146–167, 1997).

As for coumarin-based compounds, a number of structures have been proposed, including the following: Roa et al., *Synthesis* 887–888, 1981; Buu-Hoi et al., *J. Org. Chem.* 19:1548–1552, 1954; Gupta et al., *Indian J. Exp. Biol.* 23:638–640, 1985; Published PCT Application No. WO 96/31206; Verma et al., *Indian J. Chem.* 32B:239–243, 1993; lednicer et al., *J. Med. Chem.* 8:725–726, 1965; Micheli et al., *Steroids* 5:321–335, 1962; Brandt et al., *Int. J. Quantum Chemistry: Quantum Biol. Symposia* 13:155–165, 1986; Wani et al., *J Med. Chem.* 18:982–985, 1975; Pollard et al., *Steroids* 11:897–907, 1968.

Accordingly, there is a need in the art for estrogen antagonists and agonists generally, and more specifically for compounds that inhibit cytokines, particularly IL-6, including pharmaceutical compositions containing such compounds as well as methods relating to the use thereof. There is also a need for compounds that selectively modulates ER-β. The present invention fulfills these needs, and provide; other related advantages.

SUMMARY OF THE INVENTION

In brief, the present invention is generally directed to estrogen antagonists and/or agonists, including pharmaceutical compositions containing the same, as well as to methods for treating estrogen-related condition. Such conditions are more specifically discussed below, and generally include (but are not limited to) obesity, breast cancer, osteoporosis, endometriosis, cardiovascular disease, prostate cancer, menopausal syndromes, hair loss (alopecia), type-II diabetes, Alzheimer's disease, urinary incontinence, GI tract conditions, spermatogenesis, vascular protection after injury, endometriosis, learning and memory, CNS effects, plasma lipid levels, acne, cataracts, hirsutism, other solid cancers (such as colon lung. ovarian, melanoma, CNS, and renal), multiple myeloma, and lymphoma.

In a more specific embodiment, this invention is directed to compounds for inhibiting cytokines such as interleukin-6 (IL-6) and to methods relating to the treatment of conditions associated therewith, as well as pharmaceutical compositions containing one or more of the compounds of this invention. In this context, treating conditions associated with increased levels of cytokines include (but are not limited to) methods for treating cancer, arthritis and bone-resorbing diseases, particularly for reducing formation of osteoclasts and/or blocking cytokine production in the context of osteoporosis.

The compounds of this invention have the following general structure

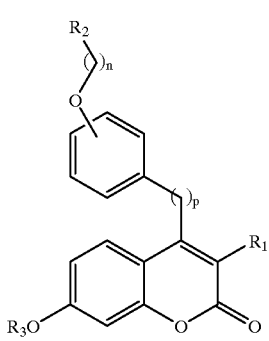

(I)

wherein $R_1$, $R_2$, $R_3$, n and p are as defined in the following detailed description, including stereoisomers, prodrugs and pharmaceutically acceptable salts thereof.

As noted above, the compounds of this invention have utility over a wide range of therapeutic and prophylactic applications, and may be used to treat a variety of diseases associated with bone resorption, as well as for treatment of cancer and arthritis. Such methods involve the administration of an effective amount of a compound of this invention, preferably in the form of a pharmaceutical composition, to an animal in need thereof (including a human).

In another embodiment, methods are disclosed for modulating cells and/or tissues that express ER-β by contacting the cell and/or tissue with an effective amount of a compound of structure (I). In an embodiment, the cell and/or tissue preferentially expresses ER-β over ER-α, such as cell and/or tissue of bone, bladder, uterus, ovary, prostate, testis, epididymis, gastrointestinal (GI) tract, kidney, breast, heart, vessel wall, immune system, lung, pituitary, hippocampus and hypothalamus.

In still a further embodiment, the present invention discloses methods for treating an estrogen-related condition by administering to an warm-blooded animal in need thereof an effective amount of a compound of structure (I) formulated as a pharmaceutical composition suitable for administration to the animal. In representative embodiments, the estrogen-related condition is breast cancer, osteoporosis, endometriosis, cardiovascular disease, hypercholesterolemia, prostatic hypertrophy, obesity, prostate cancer, menopausal syndromes, type-II diabetes, Alzheimer's disease, urinary incontinence, GI tract conditions, spermatogenesis, vascular protection after injury, endometriosis, learning and memory, CNS effects, plasma lipid levels, acne, hirsutism, other solid cancers (such as colon, lung, ovarian, testis, melanoma, CNS, and renal), multiple myeloma, lymphoma, prostatic carcinomas, obesity, hot flashes, skin effects, mood swings, memory loss, and/or adverse reproductive effects associated with exposure to environmental chemicals. In other embodiments, methods are disclosed for inhibiting a cyctokine, such as IL-6 and GM-CSF, in an animal in need thereof, as well as methods for treating cancer associated therewith.

These and other aspects of this invention will be evident upon reference to the following detailed description and attached drawings. To that end, various references are set forth herein which describe in more detail certain aspects of this invention, and which are hereby incorporated by reference in their entirety.

DETAILED DESCRIPTION OF THE INVENTION

Figure 1A:
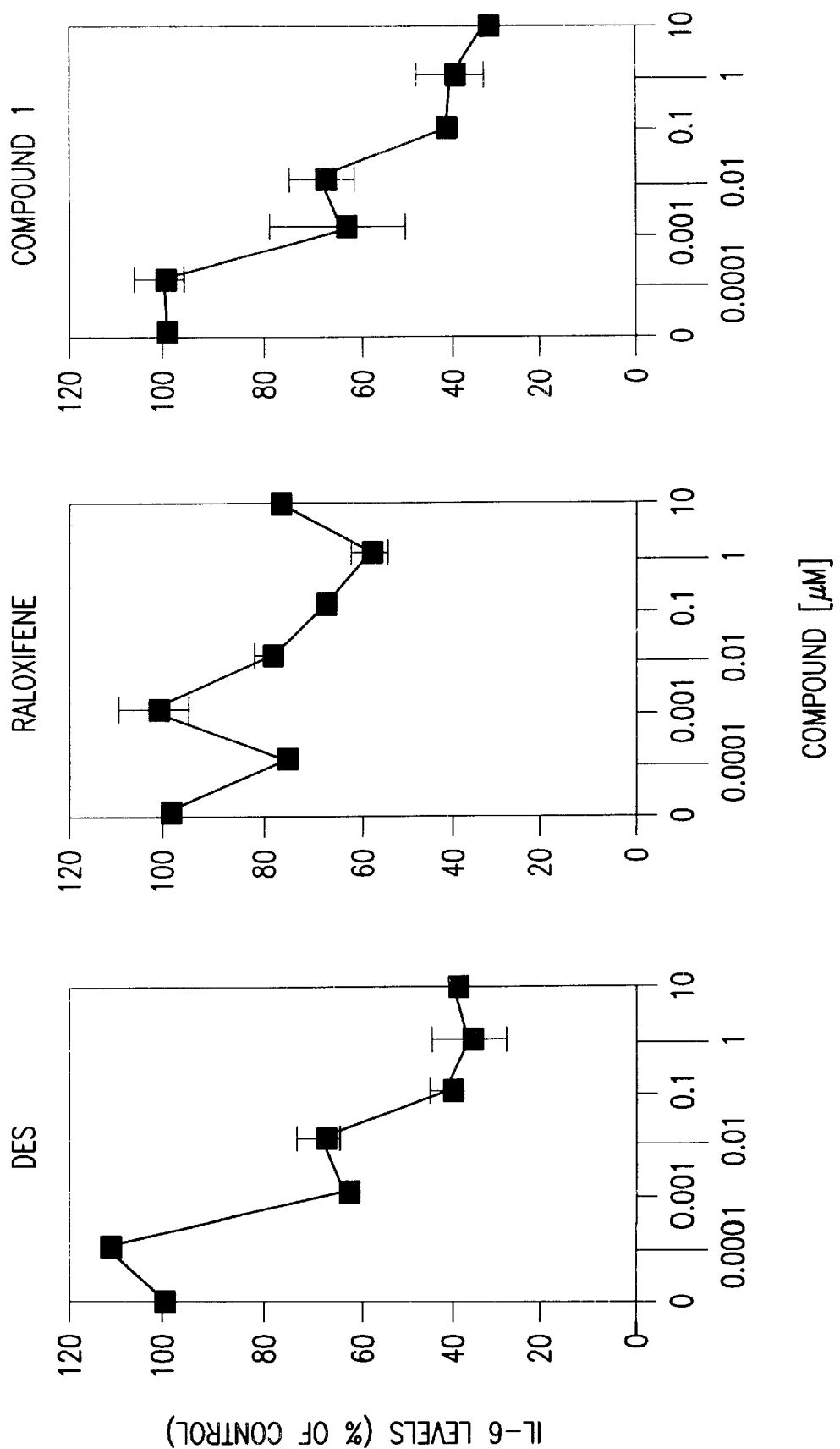
FIGS. 1A and 1B illustrate the activity of a representative compound of this invention to inhibit production of IL-6 and GM-CSF, respectively.

As mentioned above, the present invention is directed to compounds that have activity as estrogen antagonists and/or agonists, as well as pharmaceutical compositions containing one or more of such compounds and methods related to the same. As estrogen antagonists and/or agonists, the compounds of this invention have utility in the treatment of a wide range of estrogen-related conditions. In this context, the term "treatment" includes both treatment and/or prevention of an estrogen-related condition. Thus, the compounds of this invention may be administered as a therapeutic and/or prophylactic agent. An estrogen "agonist" is a compound that binds to ER and mimics the action of estrogen in one or more tissues, while an "antagonist" binds to ER and blocks the action of estrogen in one or more tissues. Further, the term "estrogen-related condition" encompasses any condition associated with elevated or depressed levels of estrogen, a selective estrogen receptor modulators (SERM), ER-α or ER-β.

Accordingly, the compounds of the present invention may also be used within a method for treating estrogen-related conditions, including (but not limited to) breast cancer, osteoporosis, endometriosis, cardiovascular disease, hypercholesterolemia, prostatic hypertrophy, prostatic carcinomas, obesity, hot flashes, skin effects, mood swings, memory loss, menopausal syndromes, hair loss (alopecia), type-II diabetes, Alzheimer's disease, urinary incontinence, GI tract conditions, spermatogenesis, vascular protection after injury, endometriosis, learning and memory, CNS effects, plasma lipid levels, acne, hirsutism, other solid cancers (such as colon, lung, ovarian, testi, melanoma, CNS, and renal), multiple myeloma, cataracts, lymphoma, and adverse reproductive effects associated with exposure to environmental chemicals.

In one aspect of this invention, it has been found that the compounds of this invention are selective estrogen receptor modulators and, more specifically, are selective to ER-β. Accordingly, in this aspect of the invention, the compounds have utility as agents for treatment of osteoporosis, hormonally regulated cancer, combination treatment of cancer (such as with taxol cisplatin or chemotherapy). women's gynecologic health issues, and health conditions resulting from exposure to environmental chemicals.

The compounds of this invention have the following general structure (I):

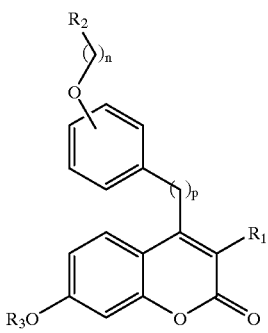

(I)

including stereoisomers, prodrugs and pharmaceutically acceptable salts thereof,
wherein:
n is 0, 1, 2, 3 or 4;
is 0, 1 or 2;
$R_1$ is an unsubstituted or substituted $C_{6-12}$aryl, $C_{7-12}$arylalky, $C_{3-12}$heterocycle or $C_{4-16}$heterocyclealkyl;
$R_2$ is $NR_aR_b$ wherein $R_a$ and $R_b$ are independently hydrogen, $G_{1-8}$alkyl, $C_{6-12}$aryl, or heterocycle, and wherein $R_a$ and $R_b$ are optionally substituted with up to three substituents independently selected from $C_{1-6}$alkyl, halogen $C_{1-6}$alkoxy, hydroxy and carboxyl;
or $R_2$ is a heterocyclic ring of the following structure:

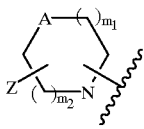

wherein
$m_1$ and $m_2$ are independently 0, 1 or 2, and both of $m_1$ and $m_2$ are not 0,
A is $CH_2$, O, S or NH,
Z represents 0, 1, 2 or 3 heterocyclic ring substituents selected from halogen $C_{1-8}$alkyl, $C_{6-12}$aryl, $C_{7-12}$arylalky, $C_{3-12}$heterocycle, or $C_{4-16}$heterocyclealkyl,
and wherein any hydrogen atom on the heterocyclic ring may, taken together with a hydrogen atom on an adjacent atom of the heterocyclic ring, form a double bond;
$R_3$ is hydrogen, $R_4$, C(=O)$R_4$, C(=O)O$R_4$, CONH$R_4$, CONR$_4$R$_5$, or SO$_2$NR$_5$R$_5$;
$R_4$ and $R_5$ are independently $C_{1-8}$alkyl, $C_{6-12}$aryl, $C_{7-12}$aralkyl, or a five- or six-membered heterocycle containing up to two heteroatoms selected from O, NR$_6$ and S(O)$_q$, wherein each of the above groups are optionally substituted with one to three substituents independently selected from $R_7$ and q is 0, 1 or 2;

$R_6$ is hydrogen or $C_{1-4}$alkyl; and
$R_7$ is hydrogen, halogen, hydroxy, $C_{1-4}$alkyl, $C_{1-4}$alkoxy, $C_{1-4}$acyloxy, $C_{1-4}$thio, $C_{1-4}$alkylsulfinyl, $C_{1-4}$alkylsulfonyl, (hydroxy)$C_{1-4}$alkyl, $C_{6-12}$ aryl, $C_{7-12}$aralkyl, COOH, CN, CONHOR$_8$, SO$_2$NHR$_8$, NH$_2$, $C_{1-4}$alkylamino, $C_{1-4}$dialkylamino, NHSO$_2$R$_8$, NO$_2$, or a five- or six-membered heterocycle, where each occurrence of R$_8$ is independently $C_{1-6}$alkyl.

As used herein, a "$C_{6-12}$aryl" is an aromatic moiety containing from 6 to 12 carbon atoms. In one embodiment, the $C_{6-12}$aryl is selected from (but not limited to) phenyl, tetralinyl, and napthalenyl.

A "$C_{7-12}$aralkyl" is an arene containing from 7 to 12 carbon atoms, and has both aliphatic and aromatic units. In one embodiment, the $C_{7-12}$aralkyl is selected from (but not limited to) benzyl, ethylbenzyl (i.e., —(CH$_2$)$_2$phenyl), propylbenzyl and isobutylbenzyl.

A "$C_{3-12}$heterocycle" is a compound that contains a ring made up of more than one kind of atom, and which contains 3 to 12 carbon atoms, including (but not limited to) pyrrolyl, furanyl, thienyl, imidazolyl, oxazolyl, thiazolyl, pyrazolyl, pyrrolidinyl, pyridinyl, pyrimidinyl and purinyl.

A "$C_{4-16}$heterocyclealkyl" is a compound that contains a $C_{3-12}$heterocycle linked to a $C_{1-8}$alkyl.

A "$G_{1-8}$alkyl" is a straight chain or branched carbon chain containing from 1 to 8 carbon atoms, including (but not limited to) methyl, ethyl, and n-propyl. Similarly, a "$C_{1-x}$alkyl has the same meaning, but wherein "x" represents the number of carbon atoms less than eight such as $C_{1-6}$alkyl.

A "substituted" $C_{1-x}$alkyl, $C_{6-12}$aryl, $C_{7-12}$aralkyl, $C_{3-12}$heterocycle, or $C_{4-16}$heterocyclealkyl moiety is a $C_{1-x}$alkyl, $C_{6-12}$aryl, $C_{7-12}$aralkyl. $C_{3-12}$heterocycle, or $C_{4-16}$heterocyclealkyl moiety having at least one hydrogen atom replaced with a substituent.

A "substituent" is a moiety selected from halogen. —OH, —R', —OR', —COOH, —COOR', —COR', —CONH$_2$, —NH$_2$, —NHR', —NR'R', —SH, —SR', —SOOR', —SOOH and —SOR', where each occurrence of R' is independently selected from an unsubstituted or substituted $C_{1-8}$alkyl, $C_{6-12}$aryl, $C_{7-12}$aralkyl, $C_{3-12}$heterocycle or $C_{4-16}$heterocyclealkyl.

A "halogen" is fluoro, chloro, bromo or iodo.

In one embodiment of this invention, A of the heterocyclic ring, $R_2$ is $CH_2$, $m_1$ is 1, and $m_2$, is 0 or 1, as represented by the following structures (i) and (ii), respectively:

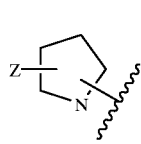

(i)

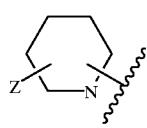

(ii)

In structures (i) and (ii) above it should be noted that the hydrogen atoms are not depicted in order to clarify that the optional Z substituent(s) may be on any atom of the heterocyclic ring, and that the point of attachment to structure (I) may be through a carbon or nitrogen atom.

Thus, in more specific embodiments of structures (i) and (ii) wherein Z is presents $R_2$ includes the following structures (iii) through (vi):

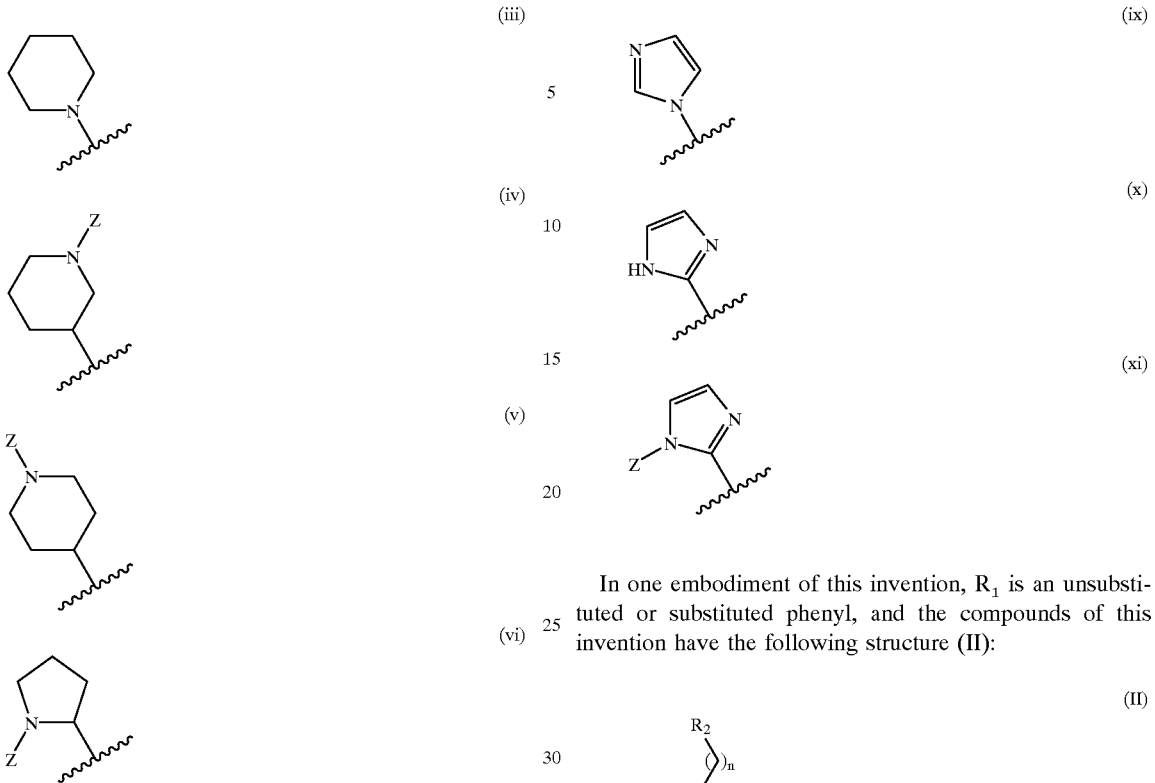

wherein Z is, for example, methyl.

In another embodiment, A of the heterocyclic ring $R_2$ is O or NH, $m_1$ is 1, and $m_2$ is 0 or 1, as represented by, for example, the following structures (vii) and (viii):

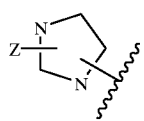

(vii)

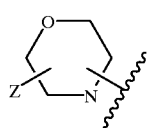

(viii)

As with structures (i) and (ii) above, in structures (vii) and (viii) the hydrogen atoms are not depicted in order to clarify that the optional Z substituent(s) may be on any atom of the heterocyclic ring, and that the point of attachment to structure (I) may be through a carbon or nitrogen atom.

In addition to the above depicted structures, any hydrogen atom of the heterocyclic ring may be taken together with a hydrogen atom attached to an adjacent heterocyclic ring atom to form a double bond. For example, with regard to structure (vii) above, corresponding unsaturated analogs include the following structures (ix), (x) and (xi):

In one embodiment of this invention, $R_1$ is an unsubstituted or substituted phenyl, and the compounds of this invention have the following structure (II):

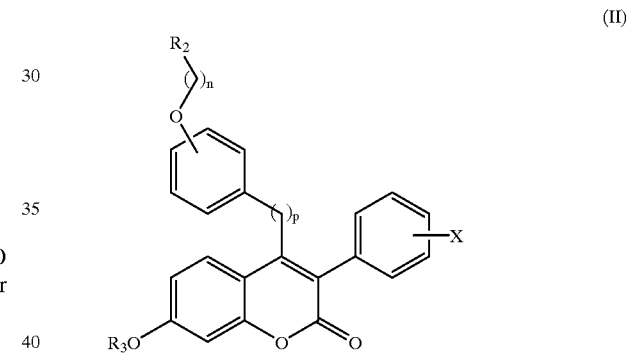

wherein X represents one or more optional substitutents as defined above, and $R_2$, $R_3$, n and p are as defined above.

In another embodiment, $R_3$ is hydrogen, as represented by structure (III):

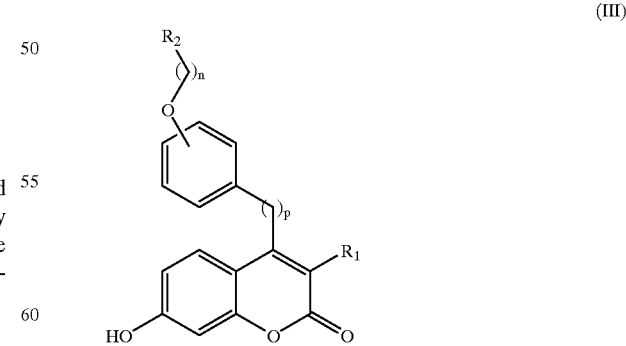

wherein $R_1$, $R_2$, n and p are as defined above.

In a more specific embodiments of structures (II) and (III), representative compounds of this invention have the following structure (IV):

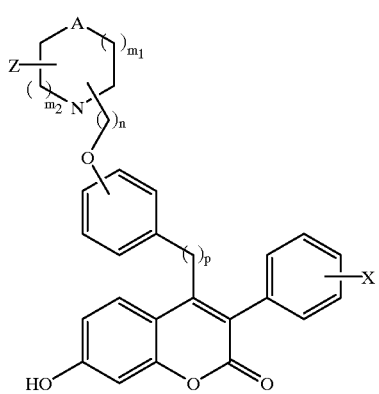

(IV)

wherein A, X, Z, $m_1$, $m_2$, n and p are as defined above.

In a further embodiment of structure (IV), $m_1$, $m_2$ and p are 1, A is $CH_2$, the optional Z substituent is not present, and n is 2, and compounds of this invention have the following, structure (V):

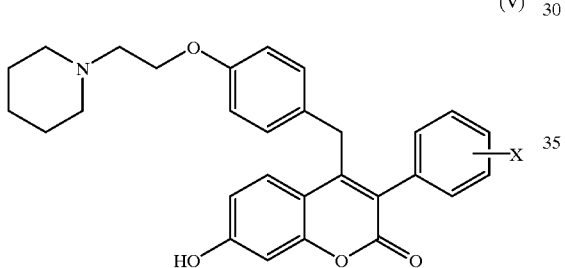

(V)

wherein X represents one or more optional substitutents as defined above.

In a more specific embodiment, X is either (a) not present or (b) represents a single substituent, such as a single stibstituent at the para position. Accordingly, representative compounds of this invention include (but are not limited to) compounds having the following structures (VIa) and (VIb):

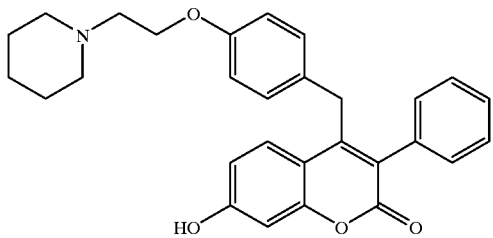

(VIa)

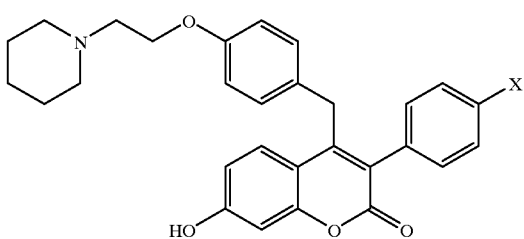

(VIb)

wherein X in structure (VIb) represents a halogen, such as fluorine or chlorine.

In a further embodiment of this invention, p is 0, and compounds of this invention have the following structure (VII):

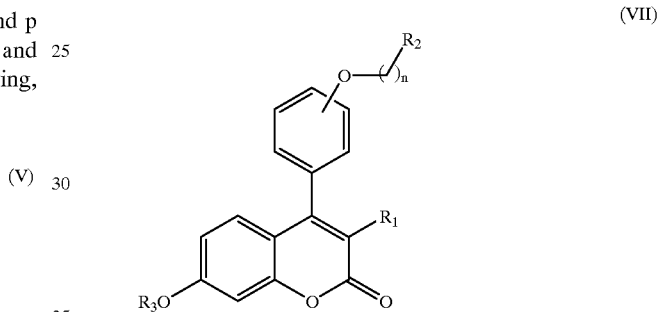

(VII)

wherein $R_1$, $R_2$, $R_3$ and n are as defined above.

In one embodiment of structure (VII), $R_1$ is an unsubstituted or substituted phenyl, and the compounds of this invention have the following structure (VIII):

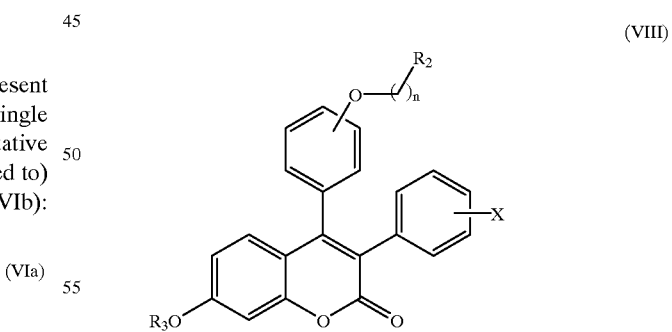

(VIII)

wherein X represents one or more optional substitutents as defined above, and $R_2$, $R_3$ and n are as defined above.

In another embodiment, $R_3$ is hydrogen as represented by structure (IX):

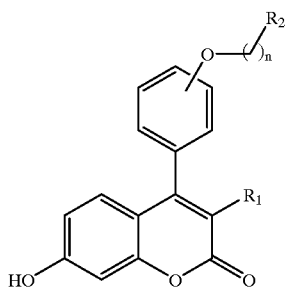

(IX)

wherein $R_1$, $R_2$ and n are as defined above.

In a more specific embodiments of structures (VIII) and (IX), representative compounds of this invention have the following structure (X):

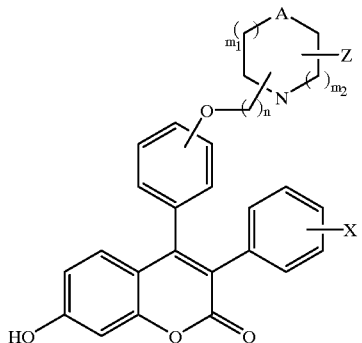

(X)

wherein A, X, Z, $m_1$, $m_2$, and n are defined above.

In a further embodiment of structure (X), $m_1$, and $m_2$, are 1, A is $CH_2$, the optional Z substituent is not present, and n is 2, and compounds of this invention have the following structure (XI):

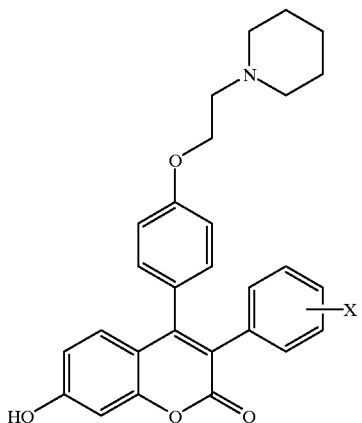

(XI)

wherein X represents one or more optional substitutents as defined above.

In a more specific embodiment, X is either (a) not present or (b) represents a single substituent, such as a single substituent at the para position. Accordingly, representative compounds of this invention include (but are not limited to) compounds having the following structures (XIa) and (XIb):

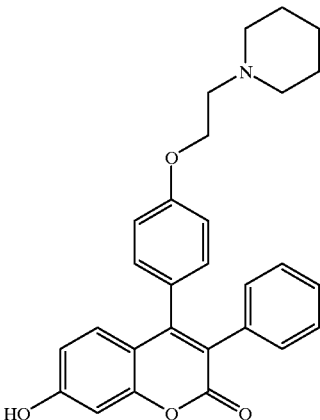

(XIa)

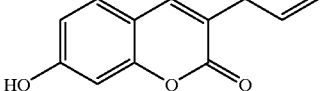

(XIb)

wherein X in structure (XIb) represents a halogen, such as fluorine or chlorine.

In the embodiment wherein p is 0, particularly when $R_3$ is hydrogen and the phenyl group at the 4-position of the coumarin ring is para-substituted, the compounds of this invention have been found to exhibit selectivity for ER-β over ER-α.

The compounds of this invention may be made by one skilled in organic synthesis by known techniques as well as by the synthetic routes disclosed herein. For example, representative compounds of this invention may be synthesized by the following general Reaction Scheme 1:

Reaction Scheme 1

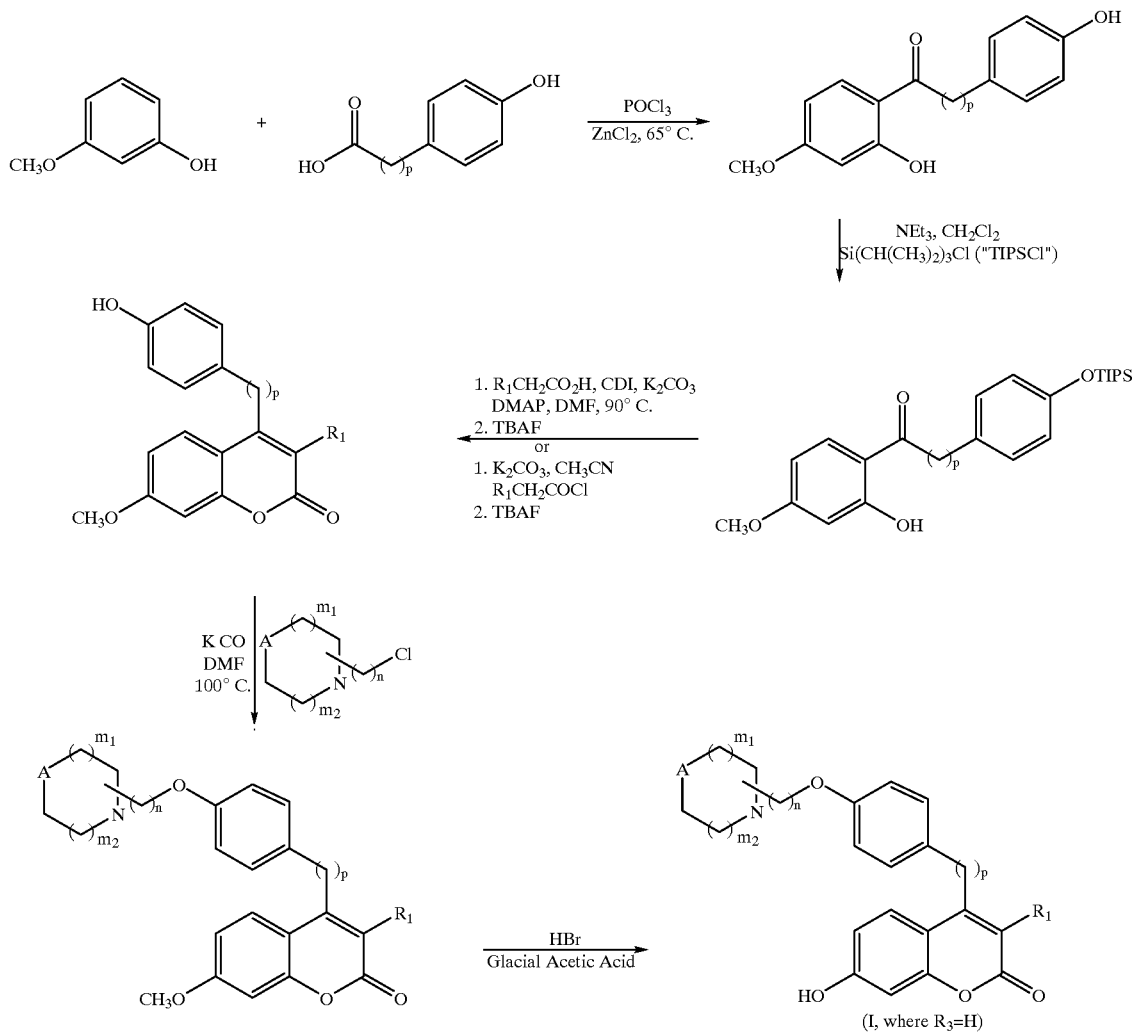

Reaction Scheme 1 yields compounds wherein $R_3$ is methyl or hydrogen, and $R_2$ is a heterocyclic ring as defined in structure (I). Further substitution at the $R_3$ position may be accomplished using an appropriately substituted phenol, or by subsequent conversion of the hydroxyl group (when $R_3$=H) using techniques known in the field of organic synthesis. Similarly, compounds of structure (I) wherein $R_2$ is $NR_aR_b$ may be made by employing the corresponding amino chloride, $R_aR_bN(CH_2)_nCl$, in place of the heterocyclic ring in the second-to-last step of Reaction Scheme 1.

More specifically, representative compounds of this invention (when $R_3$ is hydrogen and $R_2$ is piperid-1-yl) may be made by the following Reaction Scheme 2:

Reaction Scheme 2

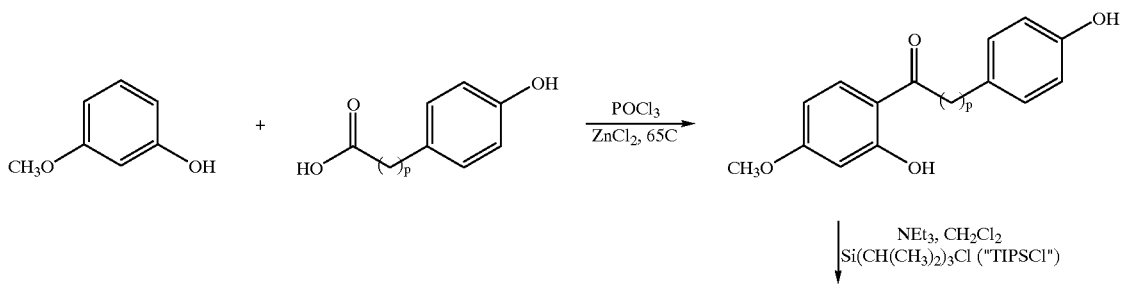

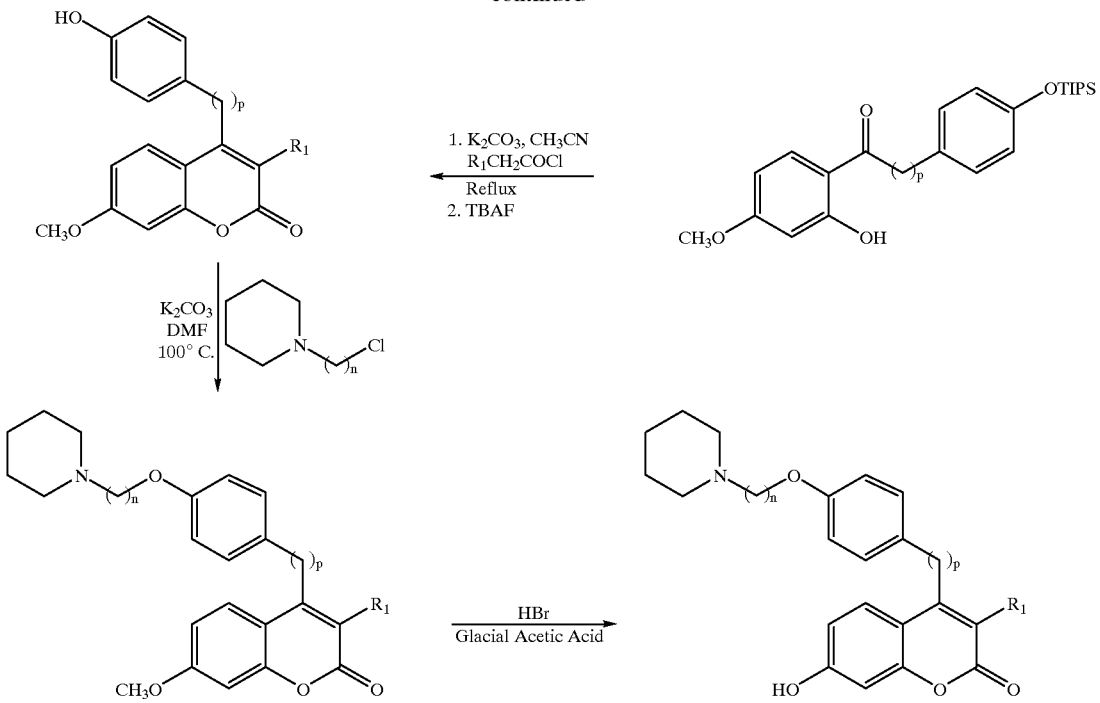

With regard to stereoisomers, the compounds of structure (I) may have chiral centers and may occur as recemates, reacemic mixtures and as individual enantiomers or diastereomers. All such isomeric forms are included within the present invention, including mixtures thereof. Furthermore, some of the crystalline forms of the compounds of structure (I) may exist as polymorphs, which are included in the present invention. In addition, some of the compounds of structure (I) may also form solvates with water or other organic solvents. Such solvates are similarly included within the scope of this invention.

Although not intending to be limited by the following theory, in the context of bone-resorbing diseases it is believed that the compounds of this invention function by blocking cytokine production and/or by inhibiting formation of osteoclasts. The cytokine IL-6 has previously been shown to be an important factor in inducing the formation of osteoclasts (Girasole et al., supra; Jilka et al. (1992), supra; Jilka et al. (1995), supra Kimble et al. (1995), supra Pacifici et al., supra; and Passeri et al., supra). Other investigators have shown that administration of the neutralizing antibody, antisense oligos, or the Sant 5 antagonist against IL-6. reduces the number of osteoclasts in trabecular bone of ovariectomized mice (Devlin et al., *J. Bone Miner* 13:393–399, 1998; Girasole et al., supra; Jilka et al. (1992), supra; and Schiller et al., *Endocrinology* 138:4567–4571, 1997), the ability of human (giant cells to resorb dentine (Ohsaki et al., *Endocrinology* 131:2229–2234, 1993; and Reddy et al., *J. Bone Min. Res.* 9:753–757, 1994), and the formation of osteoclasts in normal human bone marrow culture. It has also been found that estrogen downregulates the IL-6 promoter activity by interactions between the estrogen receptor and the transcription factors NF-κB and C/EBPβ (Stein et al., *Mol. Cell Biol.* 15:4971–4979, 1995).

Granulocyte-macrophage colony-stimulating factor (GM-CSF) has been suggested to play a role in the proliferation of osteoclastic precursor cells. In long, term cultures of human or mouse bone marrow cells or peripheral blood cells, GM-CSF promotes the formation of osteoclastic cells (Kurihara et al., *Blood* 74:1295–1302, 1989; Lorenzo et al., *J. Clin. Invest.* 80:160–164, 1987; MacDonald et al., *J. Bone Miner* 1:227–233, 1986; and Shinar et al, *Endocrinology* 126:1728–1735, 1990). Bone marrow cells isolated from postmenopausal women, or women who discontinued estrogen therapy, expressed higher levels of GM-CSF than cells from premenopausal women (Bismar et al., *J. Clin. Endocrinol. Metab.* 80:3351–3355, 1995). Expression of GM-CSF has also been shown to be associated with the tissue distribution of bone-resorbing osteoclasts in patients with erosion of orthopedic implants (Al-Saffar et al., *Anatomic Pathology* 105:628–693, 1996).

In addition, it has been found that blocking the action of IL-6 with an anti-IL-6 antibody reduces the formation of osteoclast-like cells in the human bone cell co-culture system of Example 8. This system includes immortalized human osteoblasts and premonocytic cell line U937, which are co-cultured in the game tissue culture well. Under appropriate culture conditions the osteoblasts secret IL-6 which acts on the premonocytic cells causing their differentiation into osteoclast-like cells. Thus, the co-culture system more closely reflects the physiological environment of bone, and provides a functional readout for the efficacy of the compounds known to block the production of IL-6 and leading to osteoclast activation and formation. For example, estrogen was found to suppress the production of IL-6 in the co-culture system of Example 8.

Furthermore, an anti-GM-CSF antibody was found to reduce the formation of osteoclast-like cells, and estrogen reduced the production of GM-CSF in the co-culture system of Example 8. This demonstrates that estrogen may exert its inhibitory effect on osteoclast formation and function through blocking the production of IL-6 and GM-CSF. Therefore, compounds of this invention that block IL-6 and/or GM-CSF production, or inhibit formation and function of osteoclasts, or both, are useful in the treatment of bone-resorbing diseases.

As mentioned above, cytokines are also believed to play an important role in a variety of cancers. In the context of prostate cancer, researchers have shown IL-6 to be an autocrine/paracrine growth factor (Seigall et al., supra), to enhance survival of tumors (Okamoto et al. (*Cancer Res.* 1997), supra), and that neutralizing IL-6 antibodies reduce cell proliferation (Okomoto et al. (*Endocrinology* 1997). supra; Borsellino et al., supra). IL-6 has also been reported to play a role with regard to multiple myeloma (Martinez-Maza et al., supra; Kawano et al., supra; Zhang et al., supra; Garrett et al., supra; and Klein et al., supra), renal cell carcinoma (Koo et al., supra; Tsukamoto et al., supra; and Weissglas et al., supra), and cervical carcinoma (Estuce et al., supra; Tartour et al., supra; and Iglesias et al., supra).

IL-6 is also believed to be involved in arthritis, particularly in adjuvant-, collagen- and antigen-induced arthritis (Alonzi et al., supra; Ohshima et al., supra; and Leisten et al., supra), and anti-IL-6 antibodies have been reported for treatment of arthritis (Wendling et al., supra). In addition, estrogen has been shown to induce suppression of experimental autoimmune encephalomyelitis and collagen-induced arthritis in mice (Jansson et al., supra).

Accordingly, other embodiments of the present invention include methods for treating bone-resorbing diseases generally, including (but not limited to) osteoporosis, metastatic bone cancer and hypercalcemia, osteolytic lesions with orthopedic implants, Paget's disease, and bone loss associated with hyperparathyroidism. Other conditions associated with IL-6 include various cancers and arthritis. Representative cancers are breast cancer, prostrate cancer, colon cancer, endometrial cancer, multiply myeloma, renal cell carcinoma, and cervical carcinoma. Arthritic conditions include adjuvant-, collagen-, bacterial- and antigen-induced arthritis, particularly rheumatoid arthritis.

In addition, the compounds of the present invention also act as estrogen antagonists and/or agonists, and have utility in the treatment of a wide range of estrogen-related conditions. In this context, treatment includes both treatment and/or prevention of an estrogen-related condition. Thus, the compounds of this invention may be administered as a therapeutic and/or prophylactic agent. An estrogen "agonist" is a compound that binds to ER and mimics the action of estrogen in one or more tissues, while an "antagonist" binds to ER and blocks the action of estrogen in one or more tissues. Further, the term "estrogen-related condition" encompasses any condition associated with elevated or depressed levels of estrogen, a selective estrogen receptor modulators (SERM) or ER. In this context, ER includes both ER-α and/or ER-β, as well as any isoforms, mutations and proteins with significant homology to ER.

Accordingly, the compounds of the present invention may also be used within a method for treating estrogen-related conditions, including (but not limited to) breast cancer, osteoporosis, endometriosis, cardiovascular disease, hypercholesterolemia, prostatic hypertrophy, prostatic carcinomas, obesity, hot flashes, skin effects, mood swings, memory loss, prostate cancer, menopausal syndromes, hair loss (alopecia), type-II diabetes, Alzheimer's disease, urinary incontinence, GI tract conditions, spermatogenesis, vascular protection after injury, endometriosis, learning and memory, CNS effects, plasma lipid levels, acne, cataracts, hirsutism, other solid cancers (such as colon, lung, ovarian, melanoma, CNS, and renal), multiple myeloma, lymphoma, and adverse reproductive effects associated with exposure to environmental chemicals or natural hormonal imbalances.

Compounds of the present invention that are estrogen agonists are useful for oral contraception; relief for the symptoms of menopause; prevention of threatened or habitual abortion; relief of dysmenorrhea; relief of dysfunctional uterine bleeding; relief of endometriosis; an aid in ovarian development; treatment of acne; diminution of excessive growth of body hair in women (hirsutism); the prevention and treatment of cardiovascular disease; prevention and treatment of atherosclerosis; prevention and treatment of osteoporosis; treatment of benign prostatic hyperplasia and prostatic carcinoma obesity; and suppression of post-parturn lactation. These agents also have a beneficial effect on plasma lipid levels and as such are useful in treating and preventing hypercholesterolemia. Those which are estrogen antagonists are useful as antiestrogens in, for example, breast and ovarian tissue and thus are useful in the treatment and prevention of breast and ovarian cancer.

Methods of this invention involve administering a compound of structure (I), or a pharmaceutical composition containing the one or more of the same, to an animal in need thereof in an amount sufficient to treat the disease or condition of interest. To that end, the term "treat" (or the related terms "treating" and treatment") means administration of a compound, typically in combination with an appropriate delivery vehicle or agent, to an animal that does not show signs of a disease or condition (e.g., prophylactic or preventative administration) or that does show signs of a disease or condition (e.g., curative or treatment administration). Further, the phrase "effective amount" means a dose of compound that, after a given time, results in the desired effect. For example, in the context of bone-resorbing, disease, an effective amount results in bones mass that is statistically different from that of animals treated with placebo. Similarly, for cancer and arthritis, an effective amount is an amount sufficient to produce the desired effect on the cancerous or arthritic tissue.

The methods of this invention include administration of an effective amount of a compound of structure (I), or a salt thereof, as the active ingredient. Pharmaceutically acceptable salts of the compounds of structure (I) are typically salts of non-toxic type commonly used, such as salts with organic acids (e.g., formic, acetic, trifluoroacetic, citric, maleic, tartaric, methanesulfonic, benzenesulfonic or toluenesulfonic acids), inorganic acids (e.g., hydrochloric, hydrobromic, sulfuric or phosphoric acids), and amino acids (e.g., aspartic or glutamic acids). These salts may be prepared by the methods known to chemists of ordinary skill.

The compounds of this invention may be administered to animals (including humans) orally or parenterally in the conventional form of preparations, such as capsules, microcapsules, tablets, granules, powder, troches, pills, suppositories, injections, suspensions and syrups. Suitable formulations may be prepared by methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylprrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g., sodium benzoate, sodium bisulfite, methylparaben or propylparaben), a stabilizer (e.g., citric acid, sodium citrate or acetic acid), a suspending agent (e.g., methylcellulose, polyvinyl pyrroliclone or aluminum stearate), a dispersing agent (e.g., hydroxypropylmethylcellulose), a diluent (e.g., water), and base wax (e.g., cocoa butter, white petrolatum or polyethylene glycol). The amount of the active ingredient in the medical composition may be at a level that will exercise the desired therapeutical effect; for example, about 0.1 mg to 100 mg in unit dosage for both oral and parenteral administration.

The active ingredient may be usually administered one to four times a day with a unit dosage of 0.1 mg to 100 mg, in human patients, but the above dosage may be properly varied depending on the age, body weight and medical condition of the patient and the type of administration. A preferred dose is 0.25 mg to 25 mg in human patients. One dose per day is preferred.

Pharmaceutical chemists will recognize that physiologically active compounds which one or more accessible hydroxy groups are frequently administered in the form of pharmaceutically acceptable esters. The literature concerning such compounds, such as estradiol, provides a number of instances of such esters. It is believed that such esters are metabolically cleaved in the body, and that the actual drug is the hydroxy compound itself. It is known known in pharmaceutical arts to adjust the rate or duration of action of a compound by appropriate choices of ester groups.

To this end, prodrugs are also included within the context of this invention. Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein the hydroxy group (when $R_3$=H) is bonded to any group that, when administered to a patient, cleaves to form the hydroxy group.

The pharmaceutically acceptable acid addition salts of the compounds of this invention may be formed of the compound itself, or of any of its esters, and include the pharmaceutically acceptable salts which are often used in pharmaceutical chemistry. For example, salts may be formed with inorganic or organic acids such as hydrochloric acid, hydrobromic acid, hydroiodic acid, sulfonic acids including such agents as naphthalenesulfonic, methanesulfonic and toluenesulfonic acids, sulfuric acid, nitric acid, phosphoric acid, tartaric acid, pyrosulfuric acid, metaphosphoric acid, succinic acid, formic acid, phthalic acid, lactic acid and the like, most preferable with hydrochloric acid, citric acid, benzoic acid, maleic acid, acetic acid and propionic acid. It is usually preferred to administer a compound of this invention in the form of an acid addition salt, as it is customary in the administration of pharmaceuticals bearing a basic group.

The compounds of this invention, as discussed above, are very often administered in the form of acid addition salts. The salts are conveniently formed, as is usual in organic chemistry, by reacting the compound of this invention with a suitable acid, such as have been described above. The salts are quickly formed in high yields at moderate temperatures, and often are prepared by merely isolating the compound from a suitable acidic wash in the final step of the synthesis. The salt-forming acid is dissolved in an appropriate organic solvent, or aqueous organic solvent, such as an alkanol, ketone or ester. On the other hand, if the compound of this invention is desired in the free base form, it is isolated from a basic final wash step, according to the usual practice. A typical technique for preparing hydrochlorides is to dissolve the free base in a suitable solvent and dry the solution thoroughly, as over molecular sieves, before bubbling hydrogen chloride gas through it.

The dose of a compound of this invention to be administered to a human is rather widely variable and subject to the judgment of the attending physician. It should be noted that it may be necessary to adjust the dose of a compound when it is administered in the form of a salt, such as a laureate, the salt forming moiety of which has an appreciable molecular weight. The general range of effective administration rates of the compounds is from about 0.05 mg/day to about 100 mg/day. A preferred rate range is from about 0.25 mg/day to 25 mg/day. Of course, it is often practical to administer the daily dose of compound in portions, at various hours of the day, however, in any given case, the amount of compound administered will depend on such factors as the solubility of the active component, the formulation used and the route of administration.

The route of administration of the compounds of this invention is not critical. The compounds are known to be absorbed from the alimentary tract, and so it is usually preferred to administer a compound orally for reasons of convenience. However, the compounds may equally effectively be administered percutaneously, or as suppositories for absorption by the rectum, if desired in a given instance.

The compounds of this invention are usually administered as pharmaceutical compositions which are important and novel embodiments of the invention because of the presence of the compounds. All of the usual types of compositions may be used, including tablets, chewable tablets, capsules, solutions, parenteral solutions, troches, suppositories and suspensions. Compositions are formulated to contain a daily dose, or a convenient fraction of daily dose, in a dosage unit, which may be a single tablet or capsule or convenient volume of a liquid.

Any of the compounds may be readily formulated as tablets, capsules and the like; it is preferable to prepare solutions from water-soluble salts, such as the hydrochloride salt. In general, all of the compositions are prepared according to known methods in pharmaceutical chemistry. Capsules are prepared by mixing the compound with a suitable diluent and filling the proper amount of the mixture in capsules. The usual diluents include inert powdered substances such as starch of many different kinds, powdered cellulose, especially crystalline and microcrystalline cellulose, sugars such as fructose, mannitol and sucrose, grain flours and similar edible powders.

Tablets are prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant is typically necessary in a tablet formulation to prevent the tablet and punches from sticking in the die. The lubricant is chosen from such slippery solids as talc, magnesium and calcium stearate, stearic acid and hydrogenated vegetable oils. Tablet disintegrators are substances which swell when-wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethyl cellulose, for example, may be used as well as sodium lauryl sulfate. Tablets are often coated with sugar as a flavor and sealant, or with film-forming protecting agents to modify the dissolution properties of the tablet. The compounds may also be formulated as chewable tablets, by using large amounts of pleasant-tasting substances such as mannitol in the formulation, as is now well-established in the art.

When it is desired to administer a compound as a suppository, the typical bases may be used. Cocoa butter is a traditional suppository base, which may be modified by addition of waxes to raise its melting point slightly. Water-miscible suppository bases comprising, particularly, polyethylene glycols of various molecular weights are in wide use.

The effect of the compounds may be delayed or prolonged by proper formulation. For example, a slowly soluble pellet of the compound may be prepared and incorporated in a tablet or capsule, or as a slow-release implantable device. The technique may be improved by making pellets of several different dissolution rates and filling capsules with a mixture of the pellets. Tablets or capsules may be coated with a film which resists dissolution for a predictable period of time. Even the parenteral preparations may be made long-acting, by dissolving or suspending the compound in oily or emulsified vehicles which allow it to disperse only slowly in the serum.

The following Examples are presented by way of illustration, not limitation.

EXAMPLES

In summary. Examples 1–11 are directed to the synthesis of representative compounds of this invention. Example 12 discloses a human bone cell co-culture system for assaying compounds for their ability to block production of IL-6. Example 13 discloses the activity of a representative compound of this invention as assayed in the human bone co-culture system of Example 12. Example 14–21 presents further experimental data evidencing activity of a representative compound of this invention.

Example 1

2-(4-Hydroxybenzylacetone)-5-Methoxyphenol

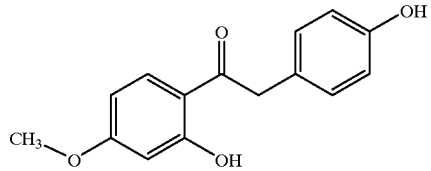

To a mixture of 3-methoxyphenol (50 g, 0.40 mol), 4-hydroxyphenylacetic acid (71 g, 0.46 mol) and $ZnCl_2$ (174 g, 1.28 mol) was added $POCl_3$ (100 ml, 1.6 mol). The mixture was stirred at 65° C. for 2 hours, poured into ice water (2 L) and stirred until the ice melted. The clear supernatant was decanted and the residue was rinsed with water (1 L) and partitioned between EtOAc and water. The organic layer was washed with brine, dried ($MgSO_4$), filtered and concentrated. The resulting oil was purified by chromatography ($SiO_2$, 20% EtOAc/n-hexane) to provide 2-(4-hydroxybenzylacetone)-5-methoxyphenol (34.1 g, 33% yield) as a white solid, mp 137–140° C.

Example 2

2-(4-Triisopropylsylyloxybenzylacetone)-5-Methoxyphenol

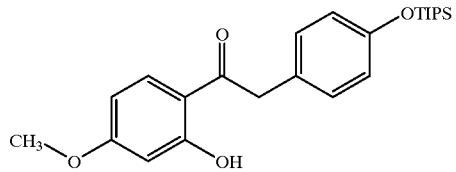

To a mixture of 2-(4-hydroxybenzylacetone)-5-methoxyphenol (10 g, 0.038 mole), $NEt_3$ (6 ml, 0.042 mole) in $CH_2Cl_2$ (50 ml) was added triisopropylsilychoride (9 ml, 0.042 mole). The mixture was stirred for 92 hours. concentrated and the residue partitioned between EtOAc and $H_2O$. The organic layer was washed with NaOH (1N). HCl (1N) and brine. The organic layer was dried ($MgSO_4$), filtered and concentrated. The residue was treated with n-hexane to provide 2-(4-Triisopropylsylyloxybenzylacetone)-5-methoxyphenol (6.2 g, 38% yield) as a white solid; mp 66–68° C.

Example 3

3-Phenyl-4-(4-Hydroxybenzyl)-7-Methozycoumarin

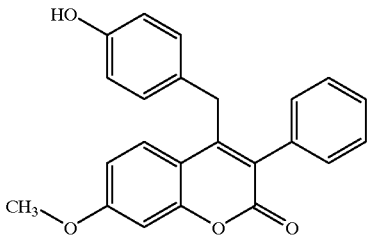

To a mixture of 2-(4-Triisopropylsylyloxybenzylacetone)-5-methoxyphenol (4 g, 9.6 mmole), $K_2CO_3$ (4 g, 29 mmole) in $CH_3CN$ (50 ml) was added phenyl acetylchloride (2.3 ml, 14 mmole). The mixture was stirred at reflux for 22 hrs, poured into $H_2O$ (0° C.) (500 ml) and extracted with EtOAc (2×). The organic layer was dried ($MgSO_4$), filtered and concentrated. The residue was stirred with $Et_2O$ and the resulting solid was filtered and recrystallized (EtOH) to give 3-phenyl-4-(4-hydroxybenzyl)-7-methoxycoumarin (0.88 g, 15% yield) as a white solid; mp 235–236° C.

Example 4

3-Phenyl-4-[4-(2-{Piperin-1-yl})Ethoxy]-Benzyl-7-Methozycoumarin

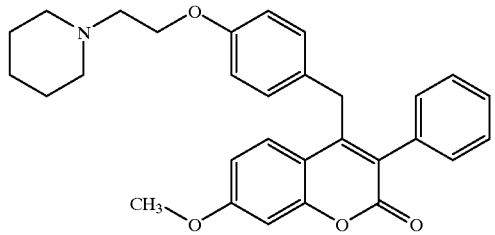

A mixture of 3-phenyl-4-(4-hydroxybenzyl)-7-methoxycoumarin (0.50 g, 1.39 mmoles), $K_2CO_3$ (0.58 g, 4.18 mmoles), 2-chloroethylpiperdine hydrochloride (0.41 g, 2.22 mmoles) and acetone (50 ml) was heated at reflux for 6 hours, the solvent was concentrated to a solid which was partitioned between EtOAc and $H_2O$. The organic layer was washed with NaOH (1H) brine dried ($MgSO_4$), filtered and concentrated. The residue was stirred with HCl (20% in EtOAc) and the solid filtered to provide 3-phenyl-4-[4-(2-{piperin-1-yl})ethoxy]-benzyl-7-methoxycoumarin (0.57 g, 87% yield); mp 171–172° C.

Example 5

3-Phenyl-4-[4-(2-{Piperidin-1-yl})Ethoxy]-Benzyl-7-Hydroxycoumarin

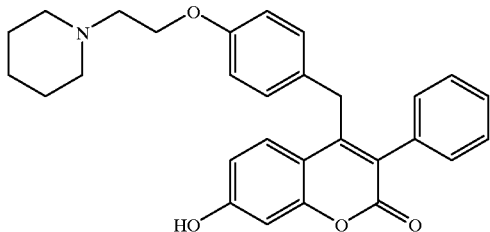

A mixture of 3-phenyl-4-[4-(2-{piperin-1-yl})ethoxy]-benzyl-7-methoxycoumarin (0.10 g, 0.20 mmole) HOAc glacial) (15 ml) and HBr (48%. 15 ml) was refluxed for 48 hours. The mixture was partitioned between EtOAc (120 ml) and NaOH (1N, 120 ml) and the aqueous layer was washed with EtOAc. The aqueous layer was then acidified (conc. HCl, pH 1-2) and filtered to provide 3-phenyl-4-[4-(2-{piperidin-1-yl})ethoxy]-benzyl-7-hydroxycoumarin (0.88 g, 99% yield); mp 160–161° C.

Example 6

3-(4-Fluorophebyl)-4-[4-(1-Methylpiperidyl-3-Oxy)]-Benzyl-7-Hydroxycoumarin

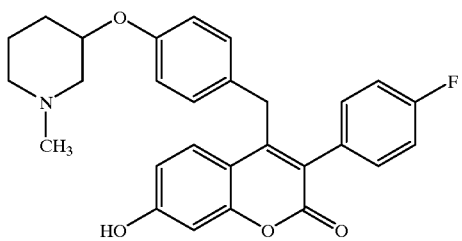

A solution 3-(4-fluorophenyl)-4-[(4-hydroxyphenyl) methyl]-7-methoxy-2H-chromen-2-one (0.27 g, 0.72 mmole), in 3 ml of CH$_2$Cl$_2$ was treated with 3-hydroxy-1-methylpiperidine (0.42 g, 3.6 mmol), triphenylphosphine (0.94 g, 3.6 mmol), and diethyl azodicarboxylate (0.65 g, 3.6 mmol). The reaction mixture was stirred for 8 hours at 25° C. then concentrated under reduced pressure. The crude product was dissolved in 4 mL, of a 1:1 solution of HBr (48%, aqueous) and glacial acetic acid. The resulting solution was warmed at 90° C. for 12 hours. The reaction mixture was concentrated and the resulting residue was neutralized with 10 mL of saturated aqueous NaHCO$_3$. The aqueous mixture was extracted with CH$_2$Cl$_2$ (3×15 mL) and the combined organic layer was dried (MgSO$_4$) then concentrated under reduced pressure. The product (106 mg, 32%) was isolated following purification by flash chromatography (SiO$_2$, CH$_2$Cl$_2$/MeOH, 10: 1).

Alternatively, 3-(4-fluorophenyl)-4-[(4-hydroxyphenyl) methyl]-7-methoxy-2H-chromen-2-one is reacted with one of the following enantiomers (a) or (b) in the presence of PPh3 and diethyl azodicarboxylate (DEAD), followed by HBr/HOAc, to yield the corresponding enantiomeric product.

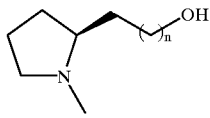

(a)

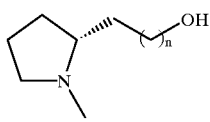

(b)

Example 7

2-Hydroxy-4-Methoxyphenyl4-Hydroxyphenyl

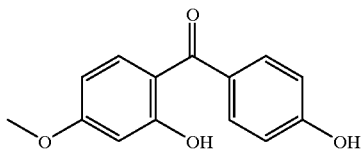

A solution of 3-methoxyphenol (2.5 g, 20.14 mmol), 4-hydroxybenzoic acid (3.2 g, 23.16 mmol), and ZnCl$_2$(8.78 g, 64.44 mmol) in 15 mL of POCl$_3$ was warmed 65° C. for 2 hours. The resulting reaction mixture was poured onto ice water (100 mL). The aqueous layer was extracted with CH$_2$Cl$_2$ and the combined organic layer was dried (MgSO$_4$) then concentrated under reduced pressure. The crude product purified by flash chromatography to provide the title compound (3.93 g, 80%) as an off-white solid (LC/MS=244 (M+H$^+$)).

Example 8

3-(4-Chlorophenyl)-4-(4-Hydroxyphenyl)-7-Methoxy-2H-Chromen-2-One 2

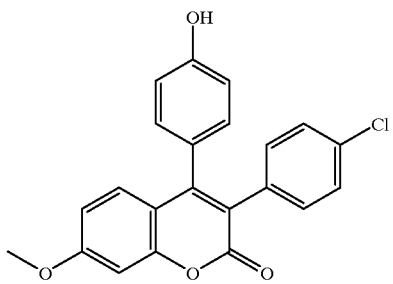

A suspension of 2-hydroxy-4-methoxyphenyl 4-hydroxyphenyl ketone (2.6 grams, 10.65 mmol), 4-chlorophenylacetic acid (4.0 g, 23.43 mmol), K$_2$CO$_3$ (4.4 g, 31.95 mmol), carbonyldiimidazole (3.8 g, 23.43 mmol), and 4-dimethylaminopyridine (0.1 g,) in 20 mL of DMF was warmed at 90° C. for 5 hours. The reaction mixture was poured into 150 mL of H$_2$O and stirred for 30 minutes. The precipitated product was collected by filtration and the purified desired product was isolated following flash chromatography (2.1 g, 52%, LC/MS=379 (M+H$^+$)).

Example 9

3-(4-Chlorophenyl)-7-Methoxy-4-[4-2-Piperidylethoxy)Phenyl]-2H-Chromen-2-One

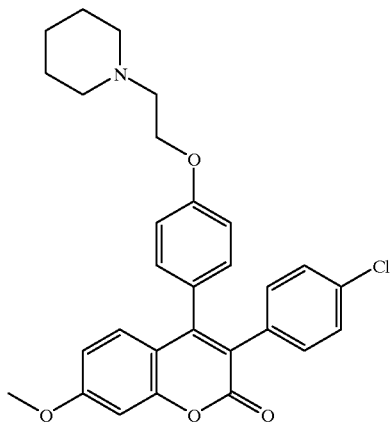

The title compound was prepared from 3-(4-chlorophenyl)-4-(4-hydroxyphenyl)-7-methoxy-2H-chromen-2-one as described in Example 4 (LC/MS=492 (M+H$^+$)).

Example 10

3-(4-Chlorophenyl)-7-Hydroxy-4-[4-(2-Piperidylethoxy)Phenyl]-2H-Chromen-2-One

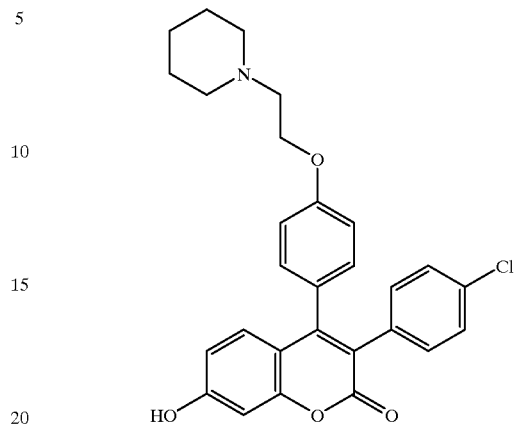

The title compound was prepared from 3-(4-chlorophenyl)-7-methoxy-4-[4-(2-piperidylethoxy)phenyl]-2H-chromen-2-one as described in Example 5 (LC/MS=476 (M+H$^+$)).

Example 11
Additional Representative Compounds

By the procedures set forth herein, the compounds of Table 1 may be prepared.

TABLE 1

Representative Compounds

| No. | $R_1$ | $R_2$† | $R_3$ | n | p | LC/MS (M + H$^+$) |
|---|---|---|---|---|---|---|
| 1 | Phenyl | piperidinyl | H | 2 | 1 | 456 |
| 2 | 4-fluorophenyl | piperidinyl | H | 2 | 1 | 474 |

TABLE 1-continued
Representative Compounds
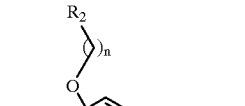
| No. | R₁ | R₂† | R₃ | n | p | LC/MS (M + H⁺) |
|---|---|---|---|---|---|---|
| 3 | 4-chlorophenyl | 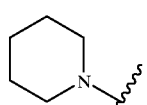 | H | 2 | 1 | 490 |
| 4 | 4-bromophenyl | 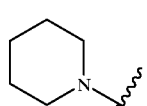 | H | 2 | 1 | 533, 535 |
| 5 | 3-chlorophenyl | 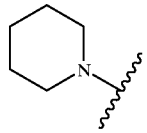 | H | 2 | 1 | 490 |
| 6 | 2-chlorophenyl | 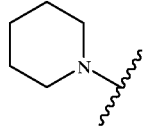 | H | 2 | 1 | 490 |
| 7 | 3-methylphenyl | 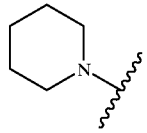 | H | 2 | 1 | 470 |
| 8 | 2-methylphenyl | 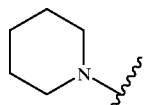 | H | 2 | 1 | 470 |
| 9 | 4-methylphenyl |  | H | 2 | 1 | 470 |

TABLE 1-continued
Representative Compounds
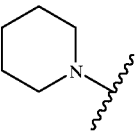
| No. | R₁ | R₂† | R₃ | n | p | LC/MS (M + H⁺) |
|---|---|---|---|---|---|---|
| 10 | 4-hydroxyphenyl | 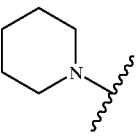 | H | 2 | 1 | 473 |
| 11 | 5-bromopyridin-3-yl | 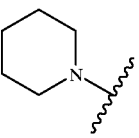 | H | 2 | 1 | 535, 537 |
| 12 | 3,4-dichlorophenyl | 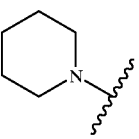 | H | 2 | 1 | 524, 526 |
| 13 | Thiophen-2-yl | 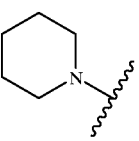 | H | 2 | 1 | 462 |
| 14 | 4-trifluoromethylphenyl | 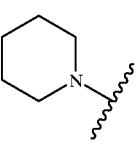 | H | 2 | 1 | 524 |
| 15 | 4-chlorophenyl | 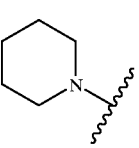 | H | 2 | 2 | 504 |
| 16 | 4-chlorophenyl | 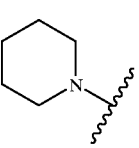 | H | 2 | 0 | 476 |

TABLE 1-continued
Representative Compounds
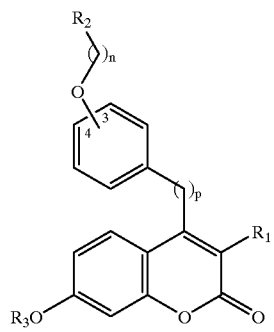
| No. | R₁ | R₂† | R₃ | n | p | LC/MS (M + H⁺) |
|---|---|---|---|---|---|---|
| 17 | Phenyl | piperidinyl | H | 2 | 1 | 458 |
| 18 | 4-fluorophenyl | N-methylpyrrolidinyl | H | 2 | 1 | 474 |
| 19 | Phenyl | piperidinyl | $SO_2N(CH_3)_2$ | 2 | 1 | 563 |
| 20 | Phenyl | piperidinyl | $CON(CH_3)_2$ | 2 | 1 | 527 |
| 21 | Phenyl | piperidinyl | CO(phenyl) | 2 | 1 | 560 |
| 22 | Phenyl | piperidinyl | $COCH_3$ | 2 | 1 | 498 |
| 23 | Phenyl | piperidinyl | $COOCH_2CH_3$ | 2 | 1 | 528 |

TABLE 1-continued
Representative Compounds
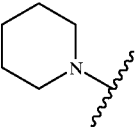
| No. | R₁ | R₂† | R₃ | n | p | LC/MS (M + H⁺) |
|---|---|---|---|---|---|---|
| 24 | 4-fluorophenyl | 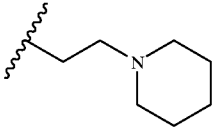 | 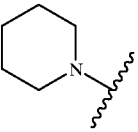 | 2 | 1 | 585 |
| 25 | 4-fluorophenyl | 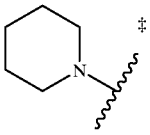 | $CH_2CH_2N(CH_3)_2$ | 2 | 1 | 574 |
| 26 | 4-chlorophenyl | 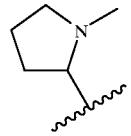 ‡ | H | 2 | 1 | 490 |
| 27 | 4-chlorophenyl | 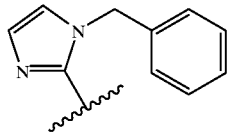 | H | 2 | 1 | 490 |
| 28 | 4-fluorophenyl | 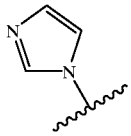 | H | 1 | 1 | 533 |
| 29 | 4-fluorophenyl | 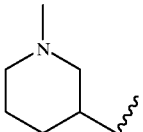 | H | 2 | 1 | 457 |
| 30 | 4-fluorophenyl |  | H | 0 | 1 | 460 |

TABLE 1-continued

Representative Compounds

| No. | $R_1$ | $R_2$† | $R_3$ | n | p | LC/MS (M + H⁺) |
|---|---|---|---|---|---|---|
| 31 | 4-fluorophenyl | 1-methylpyrrolidin-2-yl | H | 1 | 1 | 460 |
| 32 | 4-fluorophenyl | 1-methylpiperidin-4-yl | H | 0 | 1 | 460 |
| 33 | 4-chlorophenyl | piperidin-1-yl | $SO_2NH_2$ | 2 | 1 | 570 |
| 34 | 2,4-difluorophenyl | piperidin-1-yl | H | 2 | 1 | 492 |
| 35 | 2,4-dichlorophenyl | piperidin-1-yl | H | 2 | 1 | 524 |
| 36 | 4-chlorophenyl | piperidin-1-yl | $SO_2CH_3$ | 2 | 1 | 568 |
| 37 | 4-fluorophenyl | $N(CH_3)_2$ | H | 3 | 1 | 448 |

TABLE 1-continued

Representative Compounds

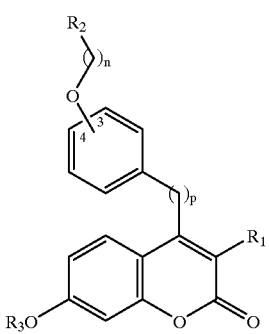

| No. | $R_1$ | $R_2^\dagger$ | $R_3$ | n | p | LC/MS $(M + H^+)$ |
|---|---|---|---|---|---|---|
| 38 | Phenyl | (diethylaminoethyl) | H | 2 | 0 | 430 |

$^\dagger$At the 4-position of the phenyl ring unless otherwise noted
$^\ddagger$At the 3-position of the phenyl ring

Example 12

Human Bone Cell Co-culture System

The generation of osteoblastic cells from normal adult femoral travecular bone from patients without evidence of metabolic bone disease was carried out as previously described (Kung Sutherland et al., Osteoporosis International 5:335–343, 1995; Wong et al., J Bone Miner 5:803–813, 1990). Bone fragments were cleaned of adherent tissue and blood and cultured for 4 weeks in medium containing Ham's F12 supplemented with 28 mM HEPES, pH 7.4, 10% FCS, 1.1 mM $CaCl_2$, 2 mM glutamine, and 1% antibiotic-antimycotic agent. Upon confluency the cells were harvested and immortalized using a retroviral vector (pLXSN) containing the neomycin resistance gene and the human papillomaviral (HPV18) F6 and E7 concogenes (International Journal of Oncology 6:167–174, 1995). The immortalized osteoblastic cells were selected in medium containing (G418 (600 μg/ml).

The human U937 moncytic cell line (cloned from the commercially available cells by serial dilution) was maintained in RPMI 1640 medium containing 10% FCS and 1% antibiotic-antimycotic agent.

The co-culture system was established as follows. Human osteoblastic cells were plated in 96-well dishes at a density of $5 \times 10^3$ cells/well, U937 cells in RPMI medium ($5 \times 10^4$ cells/well) were layered over the ostcoblasts. The formation of osteoclast-like cells was induced with 100 nM PMA. To determine the effects of compounds or the neutralizing antibodies to IL-6 (Sigma) and GM-CSF (Pharmingen) on the formation of osteoclast-like cells, the compounds or the antibodies were added 30 minutes prior to the addition of PMA. The cultures were stopped after 96 hrs and processed for histochemical or immunohistochemical analyses.

Example 13

Activity of Representative Compound in the Human Bone Co-culture

The compound of Example 5 (i.e. Compound No. 1 of Table 1) was assayed in the human bone co-culture system of Example 12 and found to have an $IC_{50}$ with respect to IL-6 and GM-CSF of 10 nM and 38 nM, respectively.

Example 14

Figure 1B:
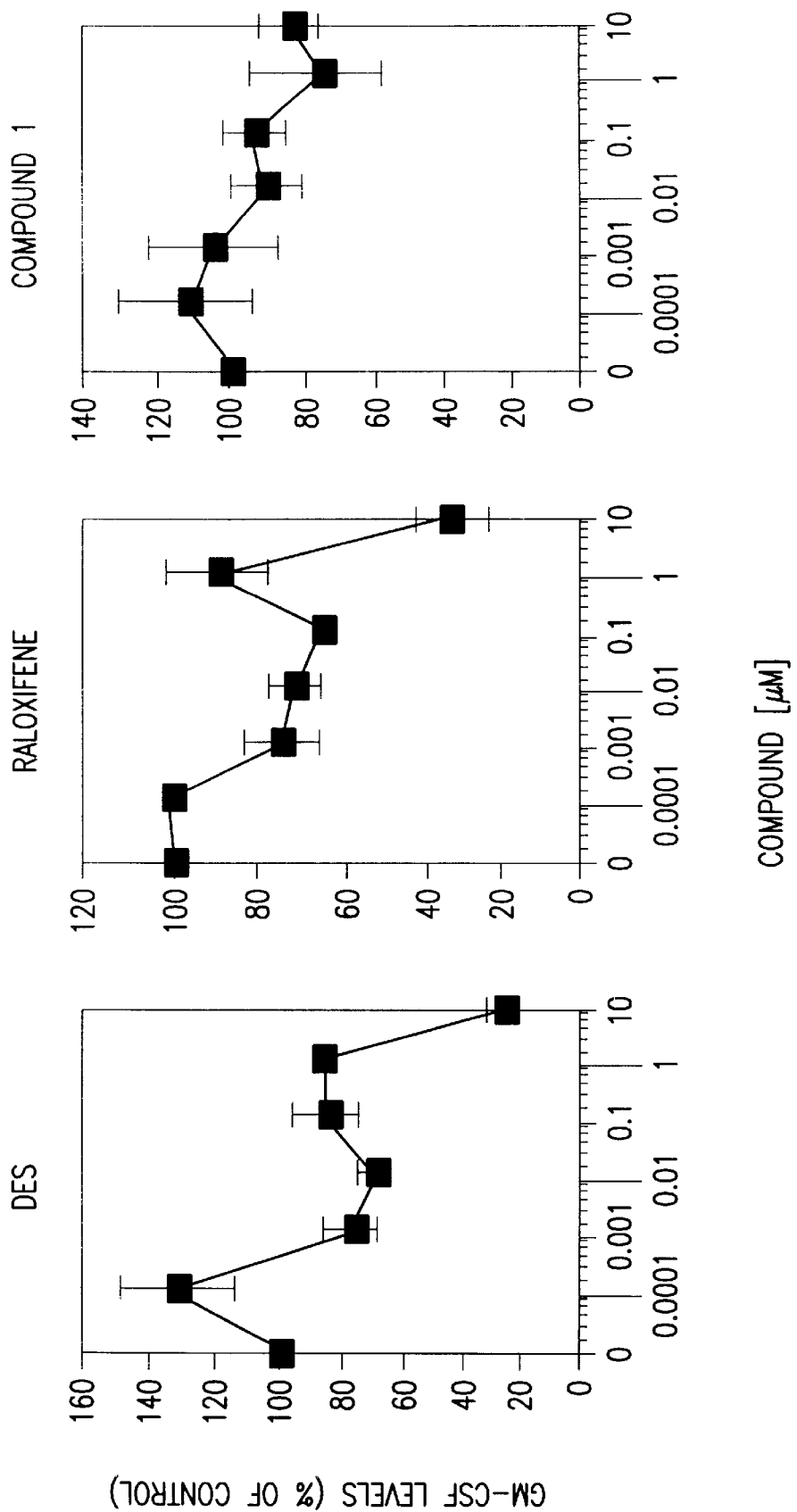

Activity of Representative Compound on IL-6 and GM-CSF Production in HOB Cells Human osteoblasts (HOB) were plated in 96-well dishes at a density of $7 \times 10^3$ cells/well in regular HOB medium (Ham's F12 supplemented with 28 mM HEPES, pH 7.4, 10% FCS, 1.1 mM $CaCl_2$, 2 mM glutamine, and 1% antibiotic-antimycotic agent). The following day, the cells were treated with Compound 1 or vehicle (0.2% DMSO) for 30 minutes prior to the addition of the combination of IL-1β (1 ng/ml) and TNF-α (10 ng/ml). Cultures were continued for 18 to 24 hrs. IL-6 and GM-CSF levels in culture medium were measured using commercially available ELISA kits (Endogen, Cambridge, Mass.). The results of this experiment are set forth in FIG. 1A for IL-6 inhibition, and FIG. 1B for GM-CSF inhibition. These figures also present the comparative data for diethylstilbestrol (DES) and Raloxifene.

Example 15

Activity of Representative Compound on IL-6 Production in RA Cells

Primary rheumatoid arthritic synoviocytes were plated in 96-well dishes at a density of $8 \times 10^3$ cells/well in phenol-red free DMEM supplemented with 2 mM glutamine, 1% antibiotic-antimycocit agent and 10% charcoal-stripped FCS. The following day, the cells were treated with Compound No. 1 or vehicle (0.2% DMSO) for 30 minutes prior to the addition of the combination of IL-123 (2 ng/ml) and TNF-α (2 ng/ml). Cultures were continued for 18 to 24 hrs. IL-6 levels in culture medium were measured using commercially available Endogen ELISAs as disclosed above.

Figure 2:
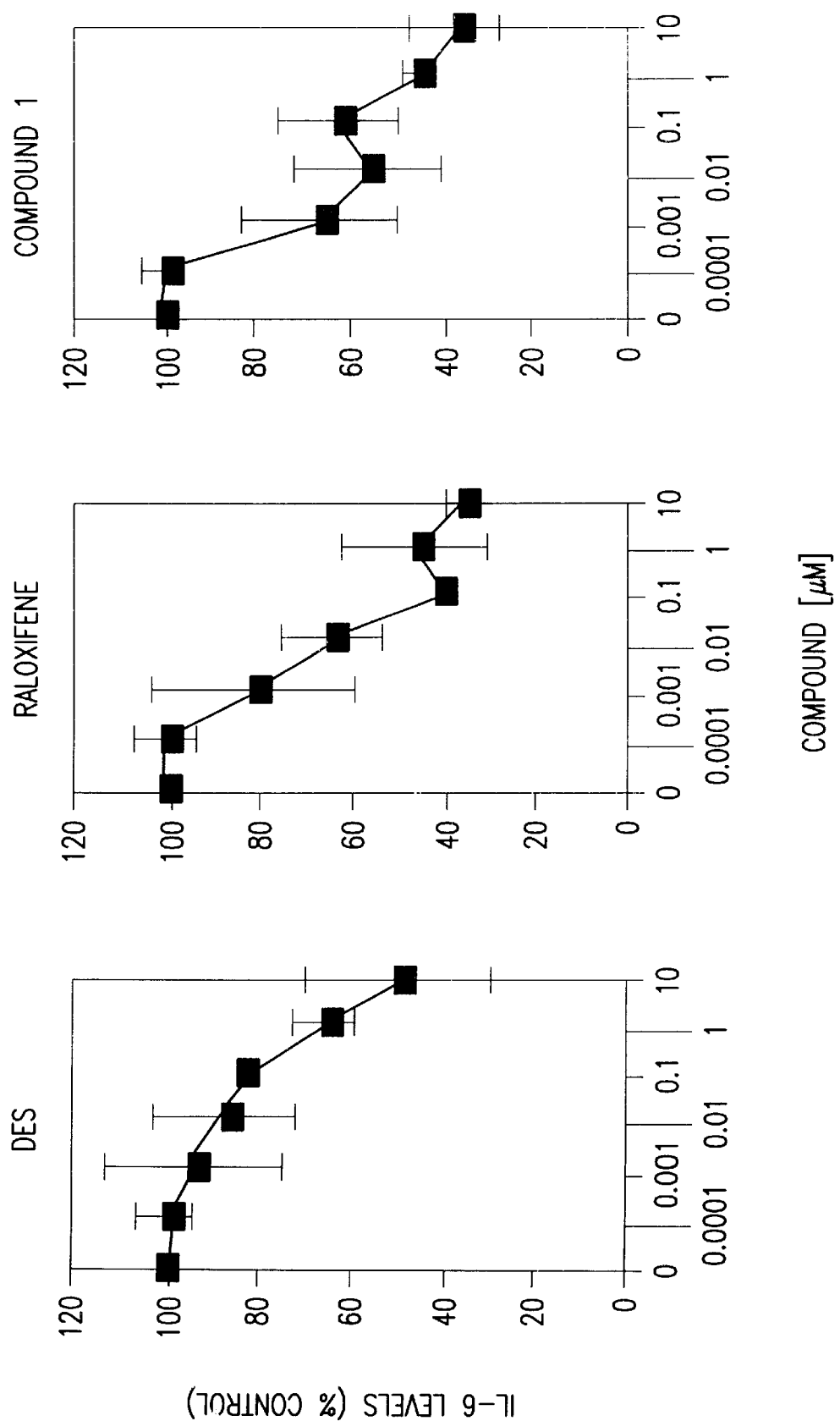
FIG. 2 illustrates the activity of a representative compound of this invention to inhibit IL-6 production in rheumatoid arthritis synoviocytes.

The results of this experiment are presented in FIG. 2, as well as the comparative activity at DES and Raloxifene.

Example 16

Figure 3:
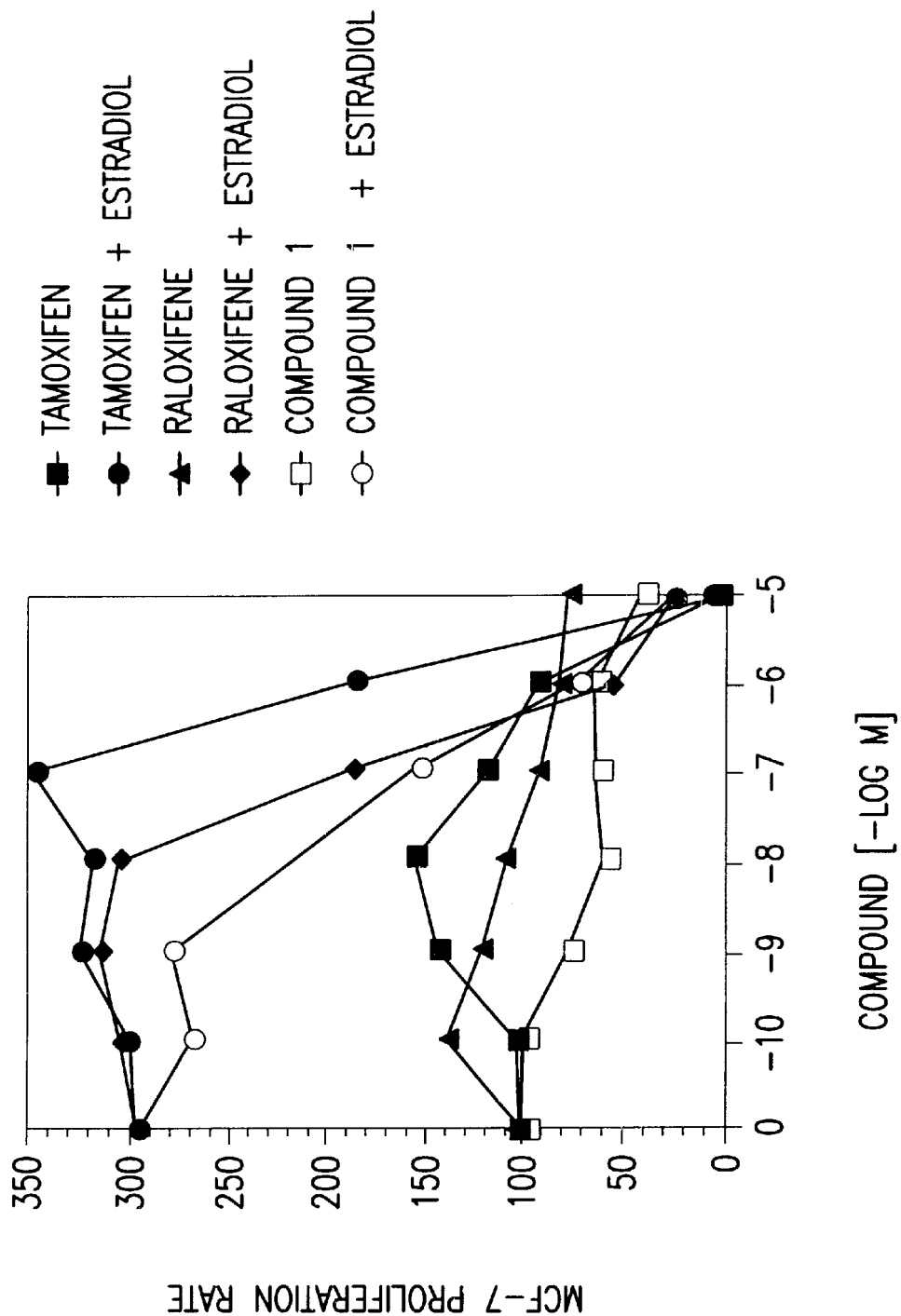
FIG. 3 illustrates the activity of a representative compound of this invention to inhibit breast cancer proliferation.

Activity of Representative Compound on Proliferation of Breast Cancer Cells MCF-7 breast carcinoma cells were plated in 24-well dishes at a density of $5 \times 10^3$ cells/well in phenol-red free DMEM:F-12 (1:1) medium containing 1% antibiotics, 0.05% β-mercaptoethanol, 0.01% ethanolamine, 0.42 ng/ml sodium selenite and 5% charcoal-stripped FCS. Compound No. 1 and vehicle (0.2% DMSO) were added the following day and refreshed with media change every 48 hours. Cultures were stopped 9 days later and proliferation assayed using the Cyquant kit (Molecular Probes, Eugene, Oreg.). The results of this experiment are presented in FIG. 3, including comparative data for Tamoxifen and Raloxifene, as well as for the combination of the same with Estradiol.

Example 17

Figure 4:
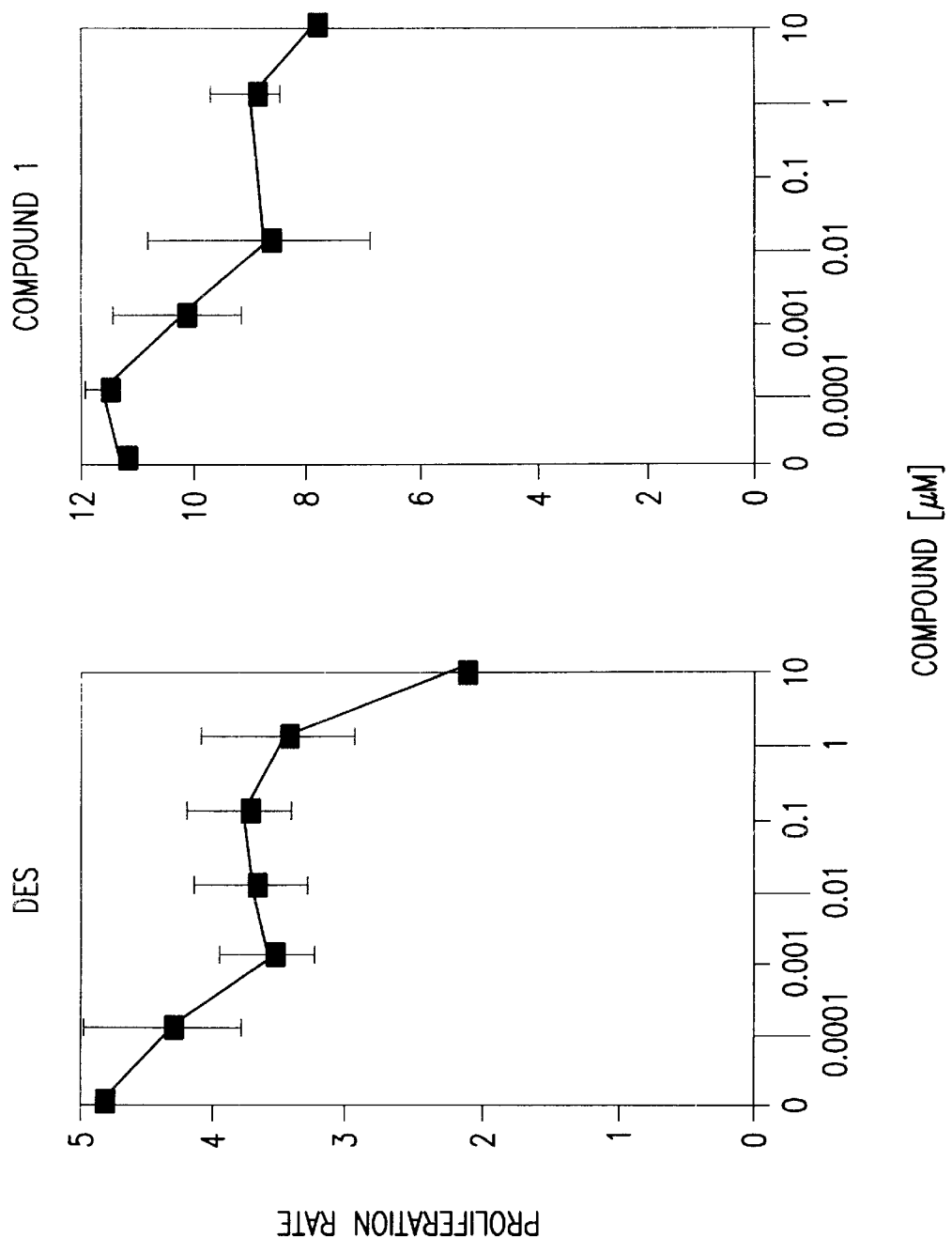
FIG. 4 illustrates the activity of a representative compound of this invention to inhibit a prostate cancer cell line.

Activity of Representative Compound on Proliferation of Prostate Carcinoma Cells DU-145 prostate carcinoma cells were plated in 96-well dishes at a density of $2 \times 10^3$ cells/well in phenol-red free MEM Eagles medium containing Earles' Balanced salts, 1% antibiotic-antimycotic agent, 2 mM glutamine, 0.1 mM non-essential amino acids 1 mM sodium pyruvate, and 10% charcoal-stripped FCS. Compound No. 1 and vehicle (0.2% DMSO) were added the following day and refreshed with medium change every 48 hrs. Cultures were stopped 5 days later and proliferation assayed using the Cyquant kit as disclosed above. The results of this experiment are presented in FIG. 4, with comparative data for DES.

Example 18

Solid Phase ER Binding Assay

Binding to human Estrogen Receptor (ER-α and ER-β) was evaluated in a solid-phase $^3$H-estradiol competition assay, as adapted from McGuire, *Cancer Res.* 38:4289–4291, 1978. Briefly, human recombinant ER-α (15 nM) or ER-β (50 nM) was immobilized to wells of 96-well microtiter plates. Binding of test compound to ER was evaluated in competition with 30 nM $^3$H-estradiol at room temperature for 1 hour. The results of this experiment, as presented in Table 2, represent the average from at least 3 different experiments. Reference compounds were tested concurrently as an integral part of each assay to ensure the validity of the results obtained.

TABLE 2

Solid Phase ER Binding $K_i$ (nM)

| Receptor Assay | Compound No. 1 (HCl salt) | Tamoxifen citrate | Raloxifene HCl | Estradiol |
|---|---|---|---|---|
| ER-α | 1.4 | 72 | 0.4 | 0.8 |
| ER-β | 7.3 | 173 | 13 | 2.5 |

Binding data for tamoxifen, raloxifene, and estradiol were found to correspond to published literature values for these compounds. Binding of Compound No. 1 (in the form of the HCl salt) to ER-α and ER-β was compared to binding of 17β-estradiol, tamoxifen citrate and raloxifeneHCl. Compound No. 1 binds with high affinity (similar to estradiol) to ER-α and ER-β Affinity for ER-β was found to be slightly lower than from ER-α, as is typical for most ER ligands

Example 19

Uterine Liability

As discussed herein, compounds that function as Selective Estrogen Receptor Modulators or SERMs are desirable. In a preferred embodiment, SERMs do not exhibit uterine liability as assessed in recognized assays, such as the immarture rat uterine bioassay (Robertson et al., *Biol. Reprod.* 54:183–196, 1996; Medlock et al., *Biol. Reprod.* 56:1239–1244, 1997; Martel et al., *Endocrinology* 139:2486–2492, 1998; Hyder et al., *Cancer Cells* 120:165–171, 1997), and the ovariectomized rat uterine bioassay (Sato et al., *FASEB J.* 10905–912, 1996; Ruenitz et al., *Bone* 23:537–542, 1998; Luo et al., *Endocrinology* 139;2645–2656, 1998; Ke et al., *Bone* 20:31–39, 1997). Both of these assays measure the effect of a particular compound on uterine wet and dry weight, and provide histological data.

Compound No. 1 was tested side-by-side with estrogen and Raloxifene.HCl in a 3-day immature rat uterine biassay using subcutaneous (s.c.) administration (Medlock et la., supra). Estrogen caused a 4.5-fold increase in uterine weight, which is the reported literature value (Ashby et al., *Regul. Toxicol. Pharmacol.* 25:226–231, 1997; Medlock et al., supra). Raloxifene.HCl caused up to 50% increase in uterine weight at the 1 mg/kg dose, which is also in agreement with published data (Ashby et al., supra). Compound No. 1 caused about a 30% increase in uterine weight, which was not statistically different from the vehicle-treated animals (i.e., PEG-400). Both Raloxifene.HCl and Compound No. 1 displayed a bell-shaped dose response, which is typically found with SERMs.

Compound No. 1 was also tested side-by-side with 17β-estradiol and Raloxifene.HCl in a 28-day uterine bioassay in ovariectomized rats (Ke et al., supra). All three compounds were administered daily by s.c, injection. Estrogen prevented the uterine weight loss caused by ovariectomy by increasing the uterine weight by 550%. These results are in agreement with published data (Grese et al., *Proc. Natl. Acad. Sci. USA* 94:14105–14110, 1997; Ashby et al., supra; Ke et al., supra). Raloxifene.HCl caused about a 70% increase in uterine weight which has been previously reported (Grese et al., supra; Ashby et al., supra). Compound No. 1 caused about a 40% increase in uterine weight which was statistically less than the Raloxifene.HCl-mediated weight increase. These results support the data from the immature rat uterine bioassay that Compound No. 1 does not exhibit significant uterine liability. Thus, this compound has significant potential for the prevention and/or treatment of cancer and osteoporosis, as well as cardiovascular diseases and neurodegenerative diseases such as Alzheimer's disease.

Example 20

Comparative Testing

Compound No. 1 was tested against a compound of Lednicer et al., *J. Med. Chem.* 8:725–726, 1965. More specifically, this reference is directed to coumarin-based compounds as purported estrogen antagonists. One of these compounds (i.e., Compound 20 of Table IV, hereinafter "L-20") has the following structure (LC/MS (M+H)$^+$=414):

Compound "L-20"

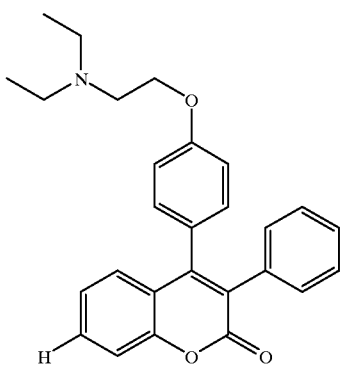

The above compound was tested against Compound No. 38 of the present invention in the ER binding assay of Example 18 and the human bone co-culture system of Example 12 for IL-6 activity. The results of these experiments are presented in Table 3.

TABLE 3

|  | ER Binding Assay | | IL-6 Activity |
|---|---|---|---|
|  | ER-α ($K_i$, μM) | ER-β ($K_i$, μM) | ($IC_{50}$, μM) |
| Compound No. 38 | 0.69 | 1.56 | 0.175 |
| "L-20" | >10 | >10 | >1 |

Example 21

ER-Selectivity in U2OS Osteosarcoma Cells

Human U2OS soteosarcoma cells (ATCC) were stably transfected with expression vectors for human full-length ER-α or ER-β, respectively, using standard molecular biology techniques. Stable subclones were generated that expressed high levels of ER-α or ER-β mRNA. The expression of ER-α and ER-β was confirmed using RNase protection analysis. The parental U2OS cells did not express any measurable amounts of either ER-α or ER-β.

Cells were plated into 96-well plates at a density of 8000 cells per well in phenol red-free media with charcoal-stripped fetal calf serum. Twenty-four hours later, cells were either treated with vehicle (0.2% DMSO) or test compound at the concentrations indicated (in 0.2% DMSO). Thirty minutes later cells were stimulated with 10 ng/ml IL-1β and 10 ng/ml TNF-α. Twenty-four hours later the media supernatant was analyzed for cytokine production (IL-6) using commercially available ELISA kits following the manufacturer's instructions. Cytokine production in the presence of vehicle (0.2% DMSO) was set to 100%.

Results of this assay are set forth in Table 4, for a number of representative compounds of this invention, as well as for the prior art test compounds. In this table, activity is expressed as $IC_{50}$ calculated by 50% inhibition relative to DMSO control (100%).

TABLE 4

Effect of Representative SERMs on Cytokines

| Compound | U2OS IL-6 ER-α $IC_{50}$ (nM) | U2OS IL-6 ER-β $IC_{50}$ (nM) | U2OS IL-6 ER-Minus $IC_{50}$ (nM) |
|---|---|---|---|
| "L-20" | >1000 | >1000 | >1000 |
| 17-β-Estradiol | 0.03 | 0.016 | >1000 |
| Raloxifene Hydrochloride | 3 | 10,000 | >1000 |
| 4-Hydroxy-Tamoxifen | 0.3–3 | >1000 | >1000 |
| Compounds No. 16 | 325 | 51 | >1000 |
| Compound No. 38 | >1000 | 165 | >10,000 |

Referring to the above table, representative compounds of this invention (e.g., Compound Nos. 16 and 38) showed specificity for ER-β over ER-α, while the prior art compounds (with the exception of 17-β-Estradiol) were selective for ER-α over ER-β.

It will be appreciated that, although specific embodiments of the invention have been described herein for purposes of illustration, various modifications may be made without departing from the spirit and scope of the invention. Accordingly, the invention is not limited except by the following claims.

What is claimed is:

1. A compound having the structure:

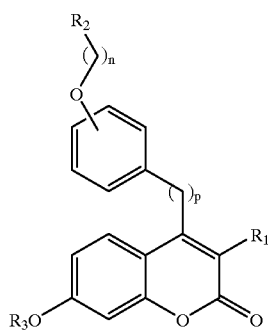

or a stereoisomer, prodrug or pharmaceutically acceptable salt thereof, wherein:

n is 0, 1, 2, 3 or 4;

p is 0;

$R_1$ is an unsubstituted or substituted $C_{6-12}$aryl, $C_{7-12}$arylalky, $C_{3-12}$heterocycle or $C_{4-16}$heterocyclealkyl;

$R_2$ is $NR_aR_b$ wherein $R_a$ and $R_b$ are independently hydrogen, $C_{1-8}$alkyl, $C_{6-12}$aryl, or heterocycle, and wherein $R_a$ and $R_b$ are optionally substituted with up to three substituents independently selected from $C_{1-6}$allyl, halogen, $C_{1-6}$alkoxy, hydroxy and carboxyl;

or R₂ is a heterocyclic ring of the following structure:

$$\text{[structure]}$$

wherein
m₁ and m₂ are independently 0, 1 or 2, and both m₁ and m₂ are not 0,
A is $CH_2$, O, S or NH,
Z represents 0, 1, 2 or 3 heterocyclic ring substituents selected from halogen, $C_{1-8}$alkyl, $C_{6-12}$aryl, $C_{7-12}$arylalky, $C_{3-12}$heterocycle, or $C_{4-6}$heterocyclealkyl,
and wherein any hydrogen atom on the heterocyclic ring may, taken together with a hydrogen atom on an adjacent atom of the heterocyclic ring, form a double bond;
$R_3$ is hydrogenate, $C(=O)R_4$, $C(=O)OR_4$, $CONHR_4$, $CONR_4R_5$, or $SO_2NR_5R_5$;
$R_4$ and $R_5$ are independently $C_{1-8}$alkyl, $C_{6-12}$aryl, $C_{7-12}$aralkyl, or a five- or six-membered heterocycle containing up to two heteroatoms selected from O, $NR_6$ and $S(O)_q$, wherein each of the above groups are optionally substituted with one to three substituents independently selected from $R_7$ and q is 0, 1 or 2;
$R_6$ is hydrogen or $C_{1-4}$ alkyl; and
$R_7$ is hydrogen, halogen, hydroxy, $C_{1-6}$alkyl, $C_{1-4}$alkoxy, $C_{1-4}$acyloxy, $C_{1-4}$thio, $C_{1-4}$alkylsulfinyl, $C_{1-4}$alkylsulfonyl, (hydroxy)$C_{1-4}$alkyl, $C_{6-12}$aryl, $C_{7-12}$aralkyl, COOH, CN, $CONHOR_8$, $SO_2NHR_8$, $NH_2$, $C_{1-4}$alkylamino, $C_{1-4}$dialkylamino, $NHSO_2R_8$, $NO_2$, or a five- or six-membered heterocycle, where each occurrence of $R_8$ is independently $C_{1-6}$alkyl.

2. The compound of claim 1 wherein $R_1$ is an unsubstituted or substituted $C_{6-12}$aryl.

3. The compound of claim 2 wherein $R_1$ is an unsubstituted or substituted phenyl.

4. The compound of claim 3 wherein $R_1$ is unsubstituted phenyl.

5. The compound of claim 3 wherein $R_1$ is substituted phenyl.

6. The compound of claim 5 wherein $R_1$ is 4-halophenyl, 4-methylphenyl, 4-hydroxyphenyl, 4-trifluorphenyl, 3-halophenyl, 2-halophenyl, 2,4-dihalophenyl, 3,4-dihalophenyl, wherein halo is fluoro chloro, bromo or iodo.

7. The compound of claim 1 wherein $R_1$ is an unsubstituted or substituted heteroaryl.

8. The compound of claim 7 wherein $R_1$ is substituted or unsubstituted pyridinyl or thiophenyl.

9. The compound of claim 1 wherein $R_1$ is an unsubstituted or substituted $C_{7-12}$arylalkyl.

10. The compound of claim 9 wherein $R_1$ is an unsubstituted or substituted benzyl.

11. The compound of claim 1 wherein $R_1$ is an unsubstituted or substituted $C_{3-12}$heterocycle or $C_{4-16}$heterocyclealkyl.

12. The compound of claim 1 wherein n is 2.

13. The compound of claim 1 wherein n is 0, 1, 3 or 4.

14. The compound of claim 1 wherein $R_3$ is hydrogen.

15. The compound of claim 1 wherein $R_3$ is $C(=O)(C_{1-8}$alkyl) or $C(=O)(C_{6-12}$aryl).

16. The compound of claim 1 wherein $R_3$ is $C(=O)O(C_{1-8}$alkyl), $SO_2NH_2$ or $CONH_2$.

17. The compound of claim 1 wherein $R_2$ is a heterocyclic ring of the following structure:

$$\text{[structure]}$$

18. The compound of claim 17 wherein m₁ and m₂ are 1.

19. The compound of claim 18 wherein A is $CH_2$.

20. The compound of claim 19 wherein $R_2$ is piperdin-1-yl.

21. The compound of claim 18 wherein A is O.

22. The compound of claim 21 wherein $R_2$ is morpholin-4-yl.

23. The compound of claim 17 wherein m₁ is 1 and m₂ is 0.

24. The compound of claim 23 wherein A is $CH_2$ and $R_2$ is imidazolidin-2-yl substituted with 0 or 1 Z substituents.

25. The compound of claim 17 wherein $R_2$ is imidazol-1-yl or imidazol-2-yl substituted with 0 or 1 Z substituents.

26. The compound of claim 1 wherein the $R_2$—$(CH_2)_n$—O— moiety is attached at the 4-position of the phenyl ring.

27. The compound of claim 1 wherein the $R_2$—$(CH_2)_n$—O— moiety is attached at the 3-position of the phenyl ring.

28. The compounds of claim 1 having the structure:

$$\text{[structure]}$$

29. The compound of claim 1 having the structure:

$$\text{[structure]}$$

wherein X represents one or more phenyl substituents.

30. The compound of claim 28 having the structure:

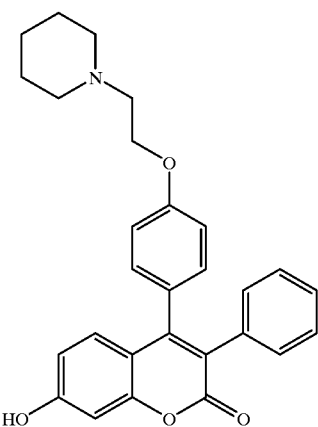

31. The compound of claim 29 having the structure:

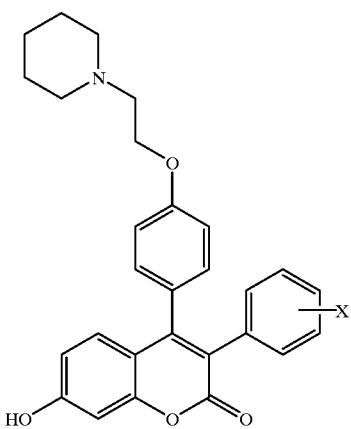

32. The compound of claim 31 having the structure:

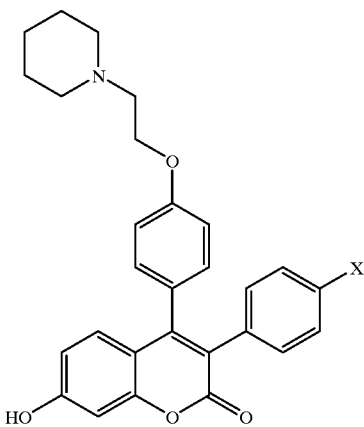

wherein X is halogen.

33. A pharmaceutical composition comprising a compound of claim 1 in combination with a pharmaceutically acceptable carrier or diluent.

34. A method for inhibiting a cytokine in an animal in need thereof, comprising administering to the animal an effective amount of the composition of claim 33.

35. The method of claim 34 wherein the cytokine is IL-6.

36. The method of claim 34 wherein the cytokine is GM-CSF.

37. A method for modulating ER-β in a cell expressing ER-β, comprising contacting the cell with an effective amount of a compound of claim 1.

38. The method of claim 37 wherein the cell preferentially expresses ER-β over ER-α.

39. The method of claim 38 wherein the cell is of bone, bladder, uterus, ovary, prostate, testis, epididymis, gastrointestinal tract, kidney, breast, eye, heart, vessel wall, immune system, lung, pituitary, hippocampus or hypothalamus cell.

40. A method for modulating ER-β in tissue expressing ER-β, comprising contacting the tissue with an effective amount of a compound of claim 1.

41. The method of claim 40 wherein the tissue preferentially expresses ER-β over ER-α.

42. The method of claim 41 wherein the tissue is tissue of bone, bladder, uterus, ovary, prostate, testis, epididymis, gastrointestinal (GI) tract, kidney, breast, eye, heart, vessel wall, immune system, lung, pituitary, hippocampus or hypothalamus.

43. A method for treating an estrogen-related condition, comprising administering to an animal in need thereof an effective amount of a pharmaceutical composition of claim 33.

44. The method of claim 43 wherein the estrogen-related condition is breast cancer, osteoporosis, endometriosis, cardiovascular disease, hypercholesterolemia, prostatic hypertrophy, prostatic carcinomas, obesity, hot flashes, skin effects, mood swings, memory loss, prostate cancer, menopausal syndromes, type-II diabetes, Alzheimer's disease, urinary incontinence, GI tract conditions, spermatogenesis, vascular protection after injury, endometriosis, learning and memory, CNS effects plasma lipid levels, acne, hirsutism, solid cancers, multiple myeloma, lymphoma, hairloss, cataracts, natural hormonal imbalances, or adverse reproductive effects associated with exposure to environmental chemicals.

45. A method for treating a bone-resorbing disease in an animal in need thereof, comprising administering to the animal an effective amount of the composition of claim 33.

46. The method of claim 39 wherein the bone-resorbing disease is osteoporosis.

47. The method of claim 39 wherein the bone-resorbing disease is metastatic bone cancer, osteolytic lesions with an orthopedic implant, Paget's disease, or bone loss associated with hyperparathyroidism.

48. A method for treating cancer associated with IL-6 in an animal in need thereof, comprising administering to the animal an effective amount of the composition of claim 33.

49. The method of claim 48 wherein the cancer is breast cancer, prostrate cancer, colon cancer, endometrial cancer, multiple myeloma, renal cell carcinoma, or cervical carcinoma.

50. A method for treating arthritis in an animal in need thereof, comprising administering to the animal an effective amount of the composition of claim 33.

51. The method of claim 50 wherein the arthritis is rheumatoid arthritis.

52. A method for modulating gene expression in a cell expressing ER-β, comprising containing the cell with an effective amount of a compound of claim 1.

53. The method of claim 52 wherein the cell is of bone, bladder, uterus, ovary, prostate, testis, epididymis gastrointestinal tract, kidney, breast, eye, heart, vessel wall, immune, system, lung, pituitary, hippocampus or hypothalamus.

54. The compound of claim 1, wherein the compound has the structure:

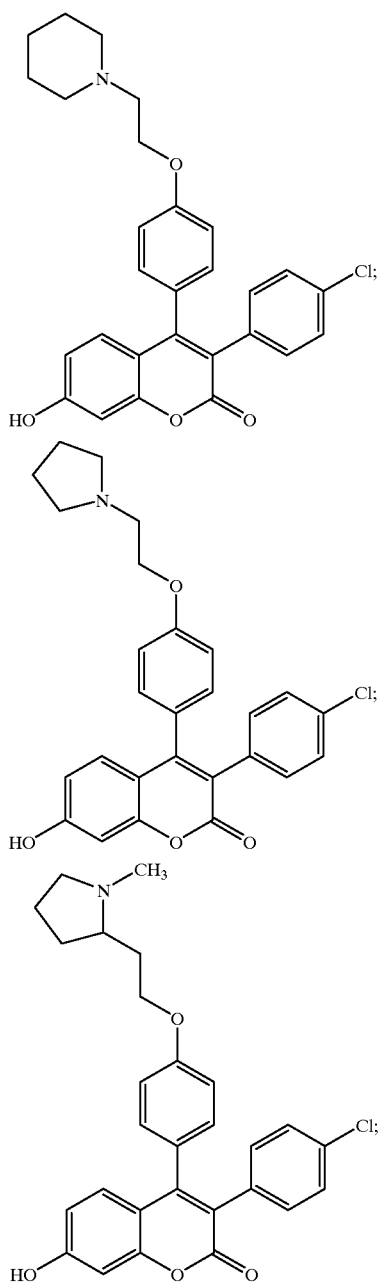

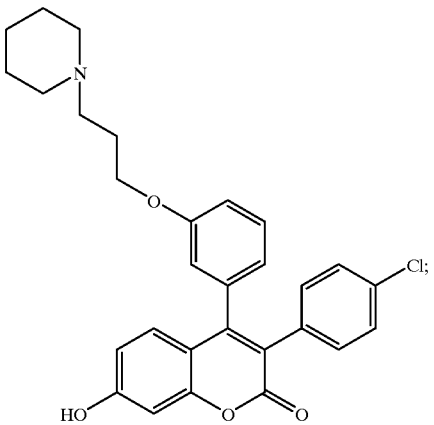

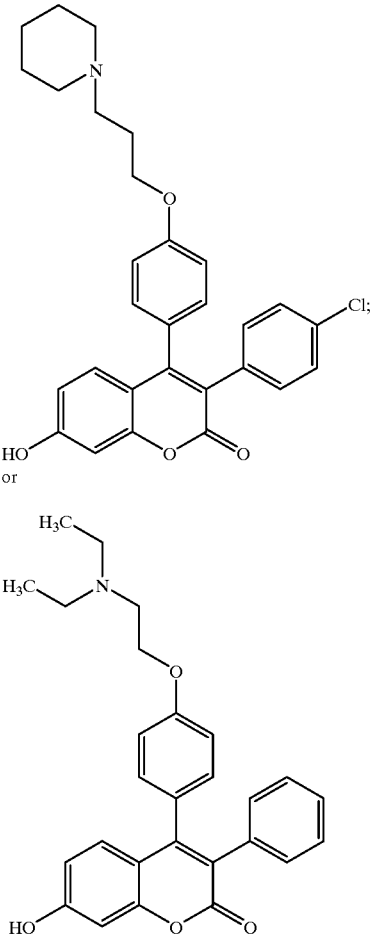

or a pharmaceutically acceptable salt thereof.

55. A pharmaceutical composition comprising a compound of claim 54 in combination with a pharmaceutically acceptable carrier or diluent.

56. A method for inhibiting a cytokine in an animal in need thereof, comprising administering to the animal an effective amount of the composition of claim 55.

57. A method for modulating ER-β in a cell expressing ER-β, comprising contacting the cell with an effective amount of the composition of claim 55.

58. A method for modulating ER-β in tissue expressing ER-β, comprising contacting the tissue with an effective amount of the composition of claim 55.

59. A method for treating an estrogen-related condition, comprising administering to an animal in need thereof an effective amount of the composition of claim 55.

60. A method for treating a bone-resorbing disease in an animal in need thereof, comprising administering to the animal an effective amount of the composition of claim 55.

61. A method for treating cancer associated with IL-6 in an animal in need thereof, comprising administering to the animal an effective amount of the composition of claim 55.

62. A method for treating arthritis in an animal in need thereof, comprising administering to the animal an effective amount of the composition of claim 55.

63. A method for modulating gene expression in a cell expressing ER-$\beta$, comprising contacting the cell with an effective amount of the composition of claim 55.

* * * * *

UNITED STATES PATENT AND TRADEMARK OFFICE
CERTIFICATE OF CORRECTION

PATENT NO. : 6,331,562 B1
DATED : December 18, 2001
INVENTOR(S) : Bhagwat et al.

It is certified that error appears in the above-identified patent and that said Letters Patent is hereby corrected as shown below:

Column 46,
Line 33, please replace "$C_{1-6}$allyl" with -- $C_{1-6}$alkyl --;
Line 33, please replace "hydrogenate" with -- hydrogen --;

Column 47,
Line 46, please insert a comma after "fluoro";

Column 50,
Line 36, please insert a comma after "CNS effects"; and

Column 51,
Line 6, please replace "containing" with -- contacting --.

Signed and Sealed this

Thirteenth Day of August, 2002

Attest:

Attesting Officer

JAMES E. ROGAN
Director of the United States Patent and Trademark Office